(12) United States Patent
Chen et al.

(10) Patent No.: US 12,635,682 B2
(45) Date of Patent: *May 26, 2026

(54) PACKAGING ASSEMBLY FOR STORING TISSUE AND CELLULAR MATERIAL

(71) Applicant: LifeNet Health, Virginia Beach, VA (US)

(72) Inventors: Silvia Chen, Virginia Beach, VA (US); Austin Johnson, Virginia Beach, VA (US); Roberto Bracone, Virginia Beach, VA (US)

(73) Assignee: LifeNet Health, Virginia Beach, VA (US)

( * ) Notice: Subject to any disclaimer, the term of this patent is extended or adjusted under 35 U.S.C. 154(b) by 159 days.

This patent is subject to a terminal disclaimer.

(21) Appl. No.: 18/225,923

(22) Filed: Jul. 25, 2023

(65) Prior Publication Data

US 2023/0363374 A1    Nov. 16, 2023

Related U.S. Application Data

(60) Division of application No. 17/142,707, filed on Jan. 6, 2021, now Pat. No. 11,730,163, which is a
(Continued)

(51) Int. Cl.
*A61J 1/10* (2006.01)
*A01N 1/122* (2025.01)
(Continued)

(52) U.S. Cl.
CPC ............. *A01N 1/122* (2025.01); *A01N 1/146* (2025.01); *A01N 1/147* (2025.01); *A61J 1/10* (2013.01);
(Continued)

(58) Field of Classification Search
CPC .... B65D 39/0052; B65D 39/08; A61M 5/002; A61J 1/10; A01N 1/021; A01N 1/0263; A01N 1/0268
See application file for complete search history.

(56) References Cited

U.S. PATENT DOCUMENTS 4,630,448 A    12/1986  Bilstad et al.
4,998,671 A     3/1991  Leifheit
(Continued)

FOREIGN PATENT DOCUMENTS

CN    101180088 A    5/2008
CN    101479377 A    7/2009
(Continued)

OTHER PUBLICATIONS

Australian Examination Report for Australian Application No. 2014218619, dated Jan. 23, 2018, 4 pages.
(Continued)

*Primary Examiner* — Kai H Weng
(74) *Attorney, Agent, or Firm* — Matney Legal Group PLLC

(57) ABSTRACT

An improved packaging assembly for storing, distributing, treating, mixing, and dispensing tissue and/or cellular material and/or implantable material. The packaging assembly may include pouches, tubes, and a bag made of a sealable, flexible polymeric material that is open at one end and a needle-free swabable connector attached to the pouch at the other end and acting as a port to allow for the introduction or discharge of biological solutions, rinsing solution, and/or preservation solutions into the packaging assembly. The designed thickness of the wall of the packaging assembly facilitates efficient heat/cold transfer, which is useful for successful controlled rate freezing, quick thawing, and resuscitation of viable cells or tissue. The packaging assembly is also useful for combining additional biological fluids
(Continued)

with the cellular material or tissue, and for efficient mixing of the biological fluids with the tissue and/or cellular material in the assembly.

20 Claims, 18 Drawing Sheets

Related U.S. Application Data continuation of application No. 14/769,694, filed as application No. PCT/US2014/018044 on Feb. 24, 2014, now Pat. No. 10,932,464.

(60) Provisional application No. 61/767,858, filed on Feb. 22, 2013.

(51) Int. Cl.

| | |
|---|---|
| *A01N 1/146* | (2025.01) |
| *A01N 1/147* | (2025.01) |
| *A61M 5/00* | (2006.01) |
| *B65D 39/00* | (2006.01) |
| *B65D 39/08* | (2006.01) |

(52) U.S. Cl.
CPC ......... *A61M 5/002* (2013.01); *B65D 39/0052* (2013.01); *B65D 39/08* (2013.01)

(56) References Cited

U.S. PATENT DOCUMENTS

| | | | |
|---|---|---|---|
| 5,098,636 | A | 3/1992 | Balk |
| 5,209,745 | A | 5/1993 | Irr et al. |
| 5,253,754 | A | 10/1993 | Soodak |
| 5,284,655 | A | 2/1994 | Bogdansky et al. |
| 5,306,305 | A | 4/1994 | Lee |
| 5,346,061 | A | 9/1994 | Newman et al. |
| 5,366,507 | A | 11/1994 | Sottosanti |
| 5,738,671 | A | 4/1998 | Niedospial et al. |
| 5,948,426 | A | 9/1999 | Jefferies |
| 5,972,703 | A | 10/1999 | Long et al. |
| 6,089,541 | A | 7/2000 | Weinheimer et al. |
| 6,648,133 | B1 | 11/2003 | Blaschke et al. |
| 6,723,131 | B2 | 4/2004 | Muschler |
| 7,001,370 | B2 | 2/2006 | Kubalak et al. |
| 7,498,040 | B2 | 3/2009 | Masinaei et al. |
| 7,740,596 | B2 | 6/2010 | Hibner |
| 8,002,813 | B2 | 8/2011 | Scarborough et al. |
| 8,278,102 | B2 | 10/2012 | Ennis et al. |
| 8,551,068 | B2 | 10/2013 | Kyle et al. |
| 8,790,923 | B2 | 7/2014 | Ennis et al. |
| 8,883,210 | B1 | 11/2014 | Truncale et al. |
| 10,905,801 | B2 | 2/2021 | Gaskins et al. |
| 10,932,464 | B2 | 3/2021 | Chen et al. |
| 11,365,395 | B2 | 6/2022 | Wolfinbarger, Jr. et al. |
| 11,730,163 | B2 | 8/2023 | Chen et al. |
| 2001/0014831 | A1 | 8/2001 | Scarborough |
| 2003/0180263 | A1 | 9/2003 | Geistlich |
| 2005/0059952 | A1 | 3/2005 | Giuliano et al. |
| 2006/0266431 | A1 | 11/2006 | Thilly et al. |
| 2006/0270961 | A1 | 11/2006 | Costa et al. |
| 2007/0162132 | A1 | 7/2007 | Messerli |
| 2007/0191963 | A1 | 8/2007 | Winterbottom et al. |
| 2008/0214998 | A1 | 9/2008 | Kurek et al. |
| 2008/0234654 | A1 | 9/2008 | McCarthy et al. |
| 2008/0254471 | A1 | 10/2008 | Bordano |
| 2008/0262633 | A1 | 10/2008 | Williams et al. |
| 2009/0030396 | A1 | 1/2009 | Ferris |
| 2009/0191533 | A1 | 7/2009 | Bussolati |
| 2010/0034783 | A1 | 2/2010 | Son et al. |
| 2010/0303389 | A1 | 12/2010 | Armau et al. |
| 2011/0160857 | A1 | 6/2011 | Bracone et al. |
| 2012/0213754 | A1 | 8/2012 | Chapman |

FOREIGN PATENT DOCUMENTS

| | | | |
|---|---|---|---|
| CN | 101528157 | A | 9/2009 |
| CN | 102170851 | A | 8/2011 |
| KR | 20080081053 | A | 9/2008 |
| WO | 9507665 | A1 | 3/1995 |
| WO | 2010050935 | A1 | 5/2010 |
| WO | 2011146046 | A1 | 11/2011 |

OTHER PUBLICATIONS

Canadian Examination Report for Canadian Application No. 2,902,155, dated Mar. 6, 2020, 4 pages.
Canadian Examination Report for Canadian Application No. 2,902,155, dated Feb. 4, 2021, 4 pages.
Chinese Office Action for Chinese Application No. 201480022933. 9, dated Mar. 28, 2017, with English translation, 45 pages.
Chinese Office Action for Chinese Application No. 201480022933. 9, dated Dec. 26, 2017, with translation, 27 pages.
Chinese Office Action for Chinese Application No. 201480022933. 9, dated Jul. 26, 2018, with translation, 30 pages.
Chinese Office Action for Chinese Application No. 201910587405. 2, dated Aug. 28, 2020, with translation, 33 pages.
Chinese Office Action for Chinese Application No. 201910587405. 2, dated Apr. 29, 2021, with translation, 15 pages.
European Communication for European Application No. 14754747. 5, dated Jun. 9, 2017, 1 page.
European Communication for European Application No. 14754747. 5, dated Oct. 7, 2020, 4 pages.
Extended European Office Action for European Application No. 14754747.5, dated May 22, 2017, 13 pages.
Final Office Action for U.S. Appl. No. 15/494,001, mailed Apr. 22, 2020, 22 pages.
Final Office Action for U.S. Appl. No. 16/059,430, mailed Jun. 11, 2021, 12 pages.
Final Office Action for U.S. Appl. No. 16/179,173, mailed Jun. 14, 2021, 13 pages.
Indian Examination Report for Indian Application No. 3084/KOLNP/ 2015, dated May 6, 2019, with translation, 7 pages.
Korean Office Action for Korean Application No. 10-2015-7026210, mailed Mar. 4, 2020, with translation, 10 pages.
Non Final Office Action for U.S. Appl. No. 15/494,001, mailed Oct. 10, 2019, 16 pages.
Non Final Office Action for U.S. Appl. No. 16/179,173, mailed Oct. 2, 2019, 32 pages.
Non Final Office Action for U.S. Appl. No. 16/179,173, mailed Apr. 28, 2021, 14 pages.
Entire patent prosecution history of U.S. Appl. No. 14/769,694, filed Aug. 21, 2015, entitled, "Packaging Assembly for Storing Tissue and Cellular Material."
Entire patent prosecution history of U.S. Appl. No. 17/142,707, filed Jan. 6, 2021, entitled, "Packaging Assembly for Storing Tissue and Cellular Material."
Annex to Communication Re Intention to Grant for European Application No. 14754747, dated Jan. 21, 2025, 12 pages.
European Communication for European Application No. 14754747, dated Dec. 2, 2024, 7 pages.
European Communication for European Application No. 14754747, dated May 6, 2024, 4 pages.
European Communication for European Application No. 14754747, dated Nov. 4, 2022, 5 pages.
European Search Report and Search Opinion for European Application No. 25177989, dated Oct. 10, 2025, 13 pages.
Indian Hearing Notice for Indian Application No. 3084/KOLNP/ 2015, dated May 12, 2023, with translation, 3 pages.

PACKAGING ASSEMBLY FOR STORING TISSUE AND CELLULAR MATERIAL

This application is a division of U.S. patent application Ser. No. 17/142,707, filed on Jan. 6, 2021, which is a continuation of U.S. patent application Ser. No. 14/769,694, filed on Aug. 21, 2015, now U.S. Pat. No. 10,932,464, issued on Mar. 2, 2021, which is the U.S. National Phase of PCT/US2014/018044, filed Feb. 24, 2014, which claims the benefit of priority to U.S. Provisional Application No. 61/767,858, filed Feb. 22, 2013, the contents of each of which are incorporated by reference herein in their entireties.

FIELD OF THE INVENTION

This invention relates generally to improved pouches, tubes and packaging assemblies for storing, distributing, treating, mixing, and dispensing tissue and/or cellular material and/or implantable material. The invention is particularly useful for storage and cryopreservation of mammalian tissue and/or cellular material, and allows for efficient, contamination-free loading and discharge of the packaging assembly contents. The designed thickness of the wall of the packaging assembly facilitates efficient heat/cold transfer, which is useful for successful controlled rate freezing, quick thawing, and resuscitation of viable cells or tissue. The invention is also useful for combining additional biological fluids with the stored tissue and/or cellular material and for efficient mixing of the biological fluids with the tissue and/or cellular material in the assembly.

BACKGROUND OF THE INVENTION

The packaging assembly of the present invention has been designed to overcome many of the problems associated with conventional bags or containers used for storage of biological materials.

For example, conventional bags or containers have been known to be incompatible with the array of biological products stored within, and further are known to rupture during storage, particularly during low temperature cryopreservation.

Moreover, conventional bags or containers have been known to be inefficient, insofar as they do not allow for maximum product retrieval after storage and prior to use.

Additionally, conventional bags or containers do not allow for uniform distribution of biological or preservation solutions into the stored material, particularly when the stored material is tissue and/or cellular material.

Conventional bags or containers also do not allow for efficient heat/cold transfer, which is useful for successful controlled rate freezing, quick thawing, and resuscitation of viable cells or tissue.

Furthermore, conventional bags or containers do not allow for efficient mixing of biological fluids with the tissue and/or cellular material in the assembly.

There is thus a need to provide a packaging assembly that is compatible with the stored material; that maintains bag integrity, particularly during cryogenic storage; that allows for maximum product retrieval after storage; that allows for uniform distribution of biological or preservation solutions; that allows for efficient heat/cold transfer; and that allows for efficient mixing of the biological fluids with the tissue and/or cellular material in the assembly.

Accordingly, one aspect of the present invention is to overcome these limitations. Other aspects will also be apparent from the following description of the invention.

SUMMARY OF THE INVENTION

Broadly stated, according to one aspect of the invention, a packaging assembly is provided that includes a pouch which further includes a port that allows for the introduction or discharge of biological solutions and preservation solutions into or from the packaging assembly, and which also allows for the introduction or discharge of tissue and/or cellular material into or from the packaging assembly. More specifically, one or more needle-free swabable connectors may be attached to the pouch. Advantageously, the connector is both needle-free and swabable, which greatly reduces the potential for pouch rupture, allows for ease in the introduction or discharge of tissue and/or cellular material, and allows for decontaminating the outside of the packaging assembly, if necessary. The flexible pouch allows efficient mixing of the biological fluids with the tissue and/or cellular material in the assembly.

In one embodiment of the invention, the pouch may be sealed at an angle of about 5 to about 60 degrees from the end at the connector. This feature has been found useful in minimizing or eliminating dead space that could trap the tissue and/or cellular material and preclude its use.

According to another embodiment of the invention, the pouch is connected to a rigid tube, which in turn may be adapted for engagement with a plunger. The plunger may be useful for discharging tissue (thawed or unthawed) and/or cellular material from the packaging assembly and for convenient delivery of the material into a defect site during surgery. In some aspects, a plunger of the invention may be employed to ensure maximum retrieval of material from the packaging assembly.

In another embodiment, a rigid tube may be adapted for engagement within the assembly with a needle which includes one or more side channels. According to this aspect of the invention, the needle may be useful for adding cells or biological solutions to the packaging assembly. The needle may penetrate the tissue and/or cellular material in the packaging assembly and may provide for a more uniform distribution of biological solution. This embodiment of the invention may prevent damage to the stored contents or the packaging assembly.

It is to be understood that both the foregoing general description and the following detailed description are exemplary and explanatory and are intended to provide further explanation of the invention as claimed.

DETAILED DESCRIPTION OF THE INVENTION

Figures 1A, 1B:
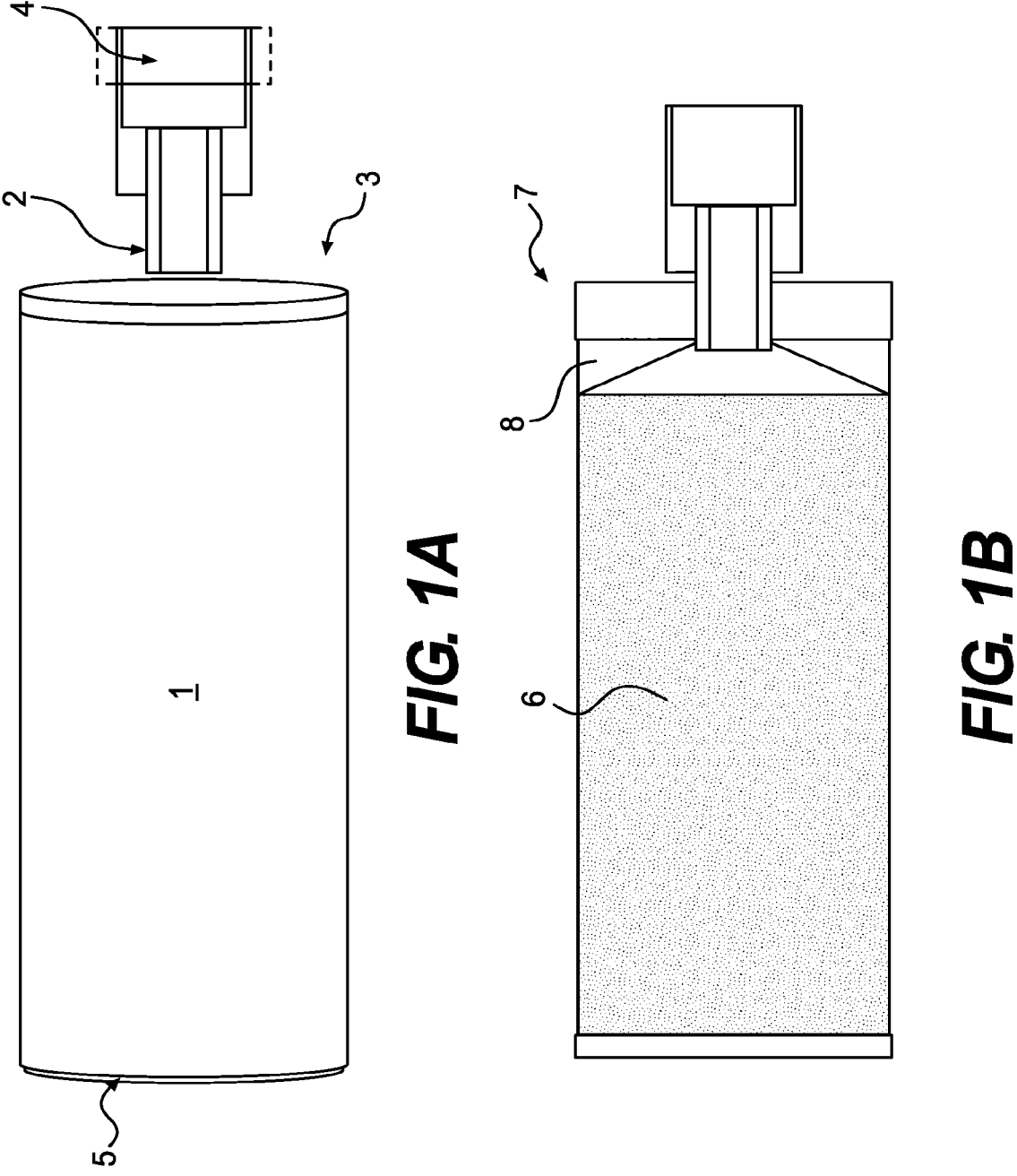
FIGS. 1A and 1B present top views of a flexible pouch of the invention both before and after the introduction of tissue and/or cellular material.

Referring more specifically to the drawings, FIGS. 1A and 1B exemplify a flexible pouch (1) made from biocompatible materials which may be bonded and sealed. The flexible pouch includes a needle-free swabable connector (2) at one end (3) and is open at the other end (5). In this embodiment, the opening (3) on the flexible pouch (1) is sealed at an angle from about 5 degrees to about 60 degrees (8) from the end of the connector to avoid the dead space that could trap cells or tissues and to allow for maximum product retrieval after storage. The angle may be from 10-50 degrees. In one embodiment, the angle is from 30-45 degrees.

In certain embodiments of the invention, said biocompatibile material may include, but is not limited to, fluorinated ethylene propylene (FEP), polytetrafluoroethylene (PTFE), perfluozlkoxy polymer resin (PFA), Ethylene tetrafluoroethylene (ETFE), Polyetheretherketone (PEEK), Polyvinylchloride (PVC), Polyethersulfone (PES), Polyethylene (PE, of various types), Polyurethane (PU), Ultem® (Polyetherimide, PEI), Cyclic Olefin Copolymer (COC), Polycarbonate (PC), Polysulfone (PS), Polypropylene (PP), BPA free polyester, ethylene-vinyl acetate copolymer, ethylene-vinyl alcohol copolymer, polyesters, polyamides, polypropylenes, polyurethanes, polyvinylidenefluoride, and a mixture of the above.

In an embodiment of the invention, the wall thickness of the flexible pouch is between about 0.0005" and about 0.010". In another embodiment of the invention, the wall thickness of the flexible pouch is between about 0.001" and about 0.007". In other embodiments of the invention, the wall thickness of the flexible pouch is between about 0.003" and about 0.006", between about 0.003" and about 0.005", between about 0.004" and about 0.006", between about 0.002" and about 0.005", about 0.004", about 0.005", and about 0.006". In certain embodiments of the invention, the wall thickness of the flexible pouch is between about 0.004" and about 0.006". This designed thickness of the wall has been found useful to maintain package integrity while facilitating efficient heat/cold transfer, which in turn may be beneficial in successful controlled rate freezing, quick thawing, and resuscitation of viable cells or tissue. In certain embodiments, the pouch may be fabricated from a pre-made extruded tube or from two sheets of biocompatible materials which are subsequently sealed together.

In certain embodiments of the invention, the connector (2) may be connected to a luer lock adaptor or connector without using any needle. The connector (2) may be used to remove or inject any biological solutions or preservation solutions.

In one embodiment, the needle-free swabable valve is the BAG ACCESS SWABABLE VALVE made by Halkey Roberts Corporation. This is just an example of a needle-free swabable valve that may be used and is not intended in any way to be limiting.

In certain embodiments of the invention, the biological solution may include, but is not limited to, normal saline, lactated ringers, lactated ringers containing dextrose, culture media, plasma, blood, bone marrow aspirate, cells from an allergenic or autologous source, phosphate buffer solution (PBS), platelet rich plasma, platelet poor plasma, growth factors, cytokines, collagen, elastin, laminin, basement membrane proteins, amniotic fluid, synovial fluid and mixtures thereof.

In certain embodiments of the invention, said preservation solutions may include, but are not limited to, saline, glycerol, hyaluronic acids, alginate, chitosan, lactated ringers, lactated ringers containing dextrose, culture media, serum, serum albumin, dimethyl sulfoxide, glucose, trehalose, vitamins, plasma, platelet rich plasma, platelet poor plasma, cryopreservation media and mixtures thereof.

In certain embodiments of the invention, the wetting agents may include, but are not limited to, water, saline solution, PBS, serum, other buffers and mixtures thereof.

The valve (4) within the connector (2) may be made of various materials, e.g., silicon or a thermoplastic elastomer, and provides the seal to prevent fluid leaking from the packaging. Under typical operations, the valve will be opened to allow fluid to be exchanged freely only when a luer lock connector is connected to the needle-free swabable connector. The sealed valve may be used to create a vacuum environment in the pouch, if desired.

Tissue and/or cellular material (6) may be loaded into the pouch from the opening at end (5). After the tissue and/or cellular material are loaded, additional biological fluids, such as preservation solutions, may be added from either end of the pouch. The opening at end (5) may then be sealed.

In certain embodiments, cellular material and/or biological fluids may also be loaded from the needle-free swabable connector (2). If the cellular material and/or biological fluids may be loaded from the needle-free swabable connector (2), the opening at end (5) may be sealed first, then the fluids or cells will be injected through the needle-free swabable connector (2). The sealed package (7) containing tissue and/or cellular material then may be placed in a secondary container and sealed again to prevent contamination.

In certain instances, the samples are stored at room temperature, in which case the sealed package (7) may be placed in a box or other container.

For cryopreserved tissue, the sealed package may be placed in a secondary container and may be frozen at a controlled freezing rate at a temperature of about −70° C. or lower, placed in a box, and stored at a temperature lower than −70° C., or in vapor phase liquid nitrogen.

Advantageously, in certain embodiments of the invention, the designed thickness of the wall of the flexible pouch (1) facilitates efficient heat/cold transfer and controlled freezing. In addition, during thawing of the cryopreserved tissue and/or cellular material, the designed thickness of the wall allows quick thaw of the tissue and/or cellular material, which is useful for maintaining cell viability.

In certain embodiments of the invention, the tissue may be viable or non viable, dry or wet, soft tissue, cartilage or bone. Cells may be of human or animal origin. Moreover, the cells may be stem cells, pluripotent, or differentiated cells.

It is understood that the pouches, tubes and packaging assemblies of the present invention may be useful for storing, distributing, treating, mixing, and dispensing tissue and/or cellular material, as well as other biological materials, fluids or solutions.

Figures 2A, 2B:
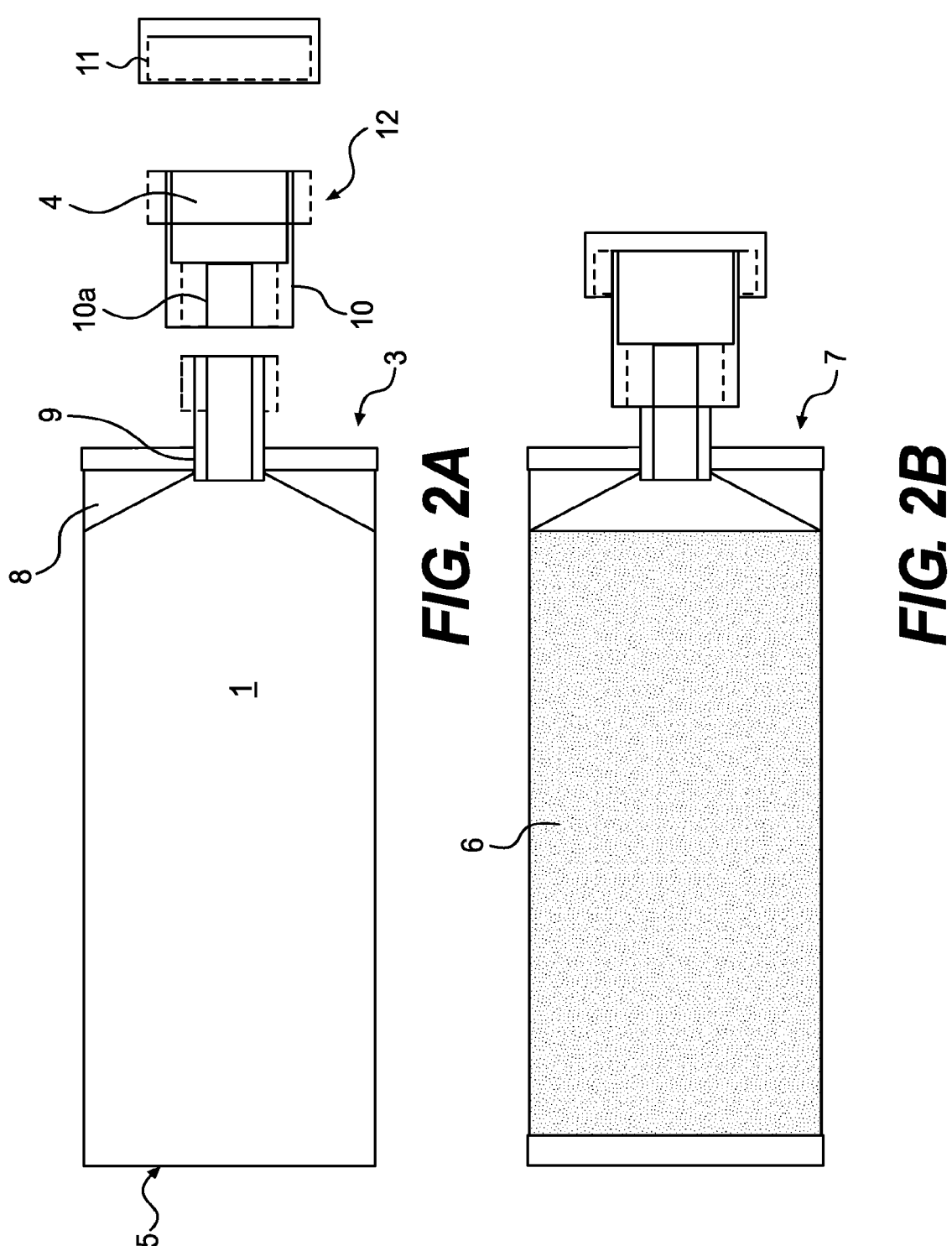
FIGS. 2A and 2B present top views of the pouch, both before and after the introduction tissue and/or cellular material. This embodiment of the invention includes a port connected to a female luer lock compatible connector and a cap.

FIGS. 2A and 2B provide another view of a flexible pouch. The flexible pouch (1) may be made from biocompatible materials which are bonded and sealed with a port (9) made of biocompatible materials, e.g., fluorinated ethylene propylene (FEP), polypropylene, polyvinylidenefluoride, or pentafluoroethylene (PTFE). The port (9) may be connected to female luer lock compatible connector (10a) of a swabable connector (10). A cap (11) may be connected to the male luer lock adaptor (12) of the swabable connector (10) to help prevent or avoid any potential contamination on the swabable connector (10).

In certain embodiments of the invention, the opening at end (3) on the flexible pouch (1) may be sealed at an angle of about 5 degrees to about 60 degrees (8) from the end of the connector to avoid the dead space that could trap tissue and/or cellular material and ensure maximum product retrieval.

The connector (10) may be connected to a luer lock adaptor or connector without using any needle. The connector (10) may be used to remove or inject biological solutions, preservation solutions, or a rinsing solution.

In one aspect, cellular material and/or biological fluids may also be loaded from the needle-free swabable connector (10). If the cellular material and/or biological fluids will be loaded from the needle-free swabable connector (10), the opening (5) may be sealed first, the fluids or cells may be injected through the needle-free swabable connector (10), and then the cap (11) will be connected to the connector (10) to prevent any potential contamination. The sealed package (7) containing tissue and/or cellular material may be placed in a secondary container and sealed again to further prevent contamination.

Figure 3A:
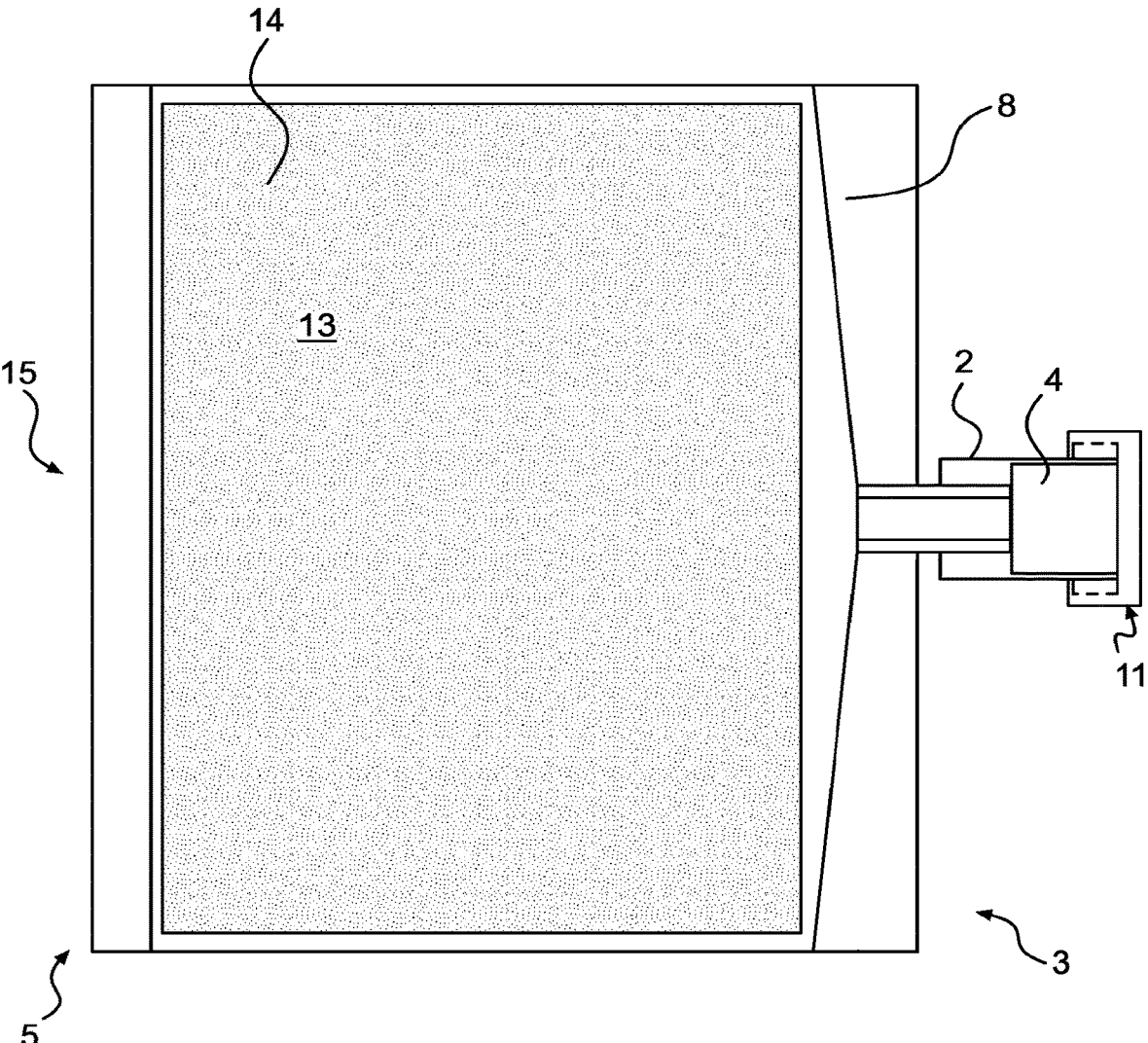
FIGS. 3A and 3B present top views of an embodiment of a large flexible pouch. The pouch is bonded and sealed with a needle-free swabable connector at one end.
Figure 3B:
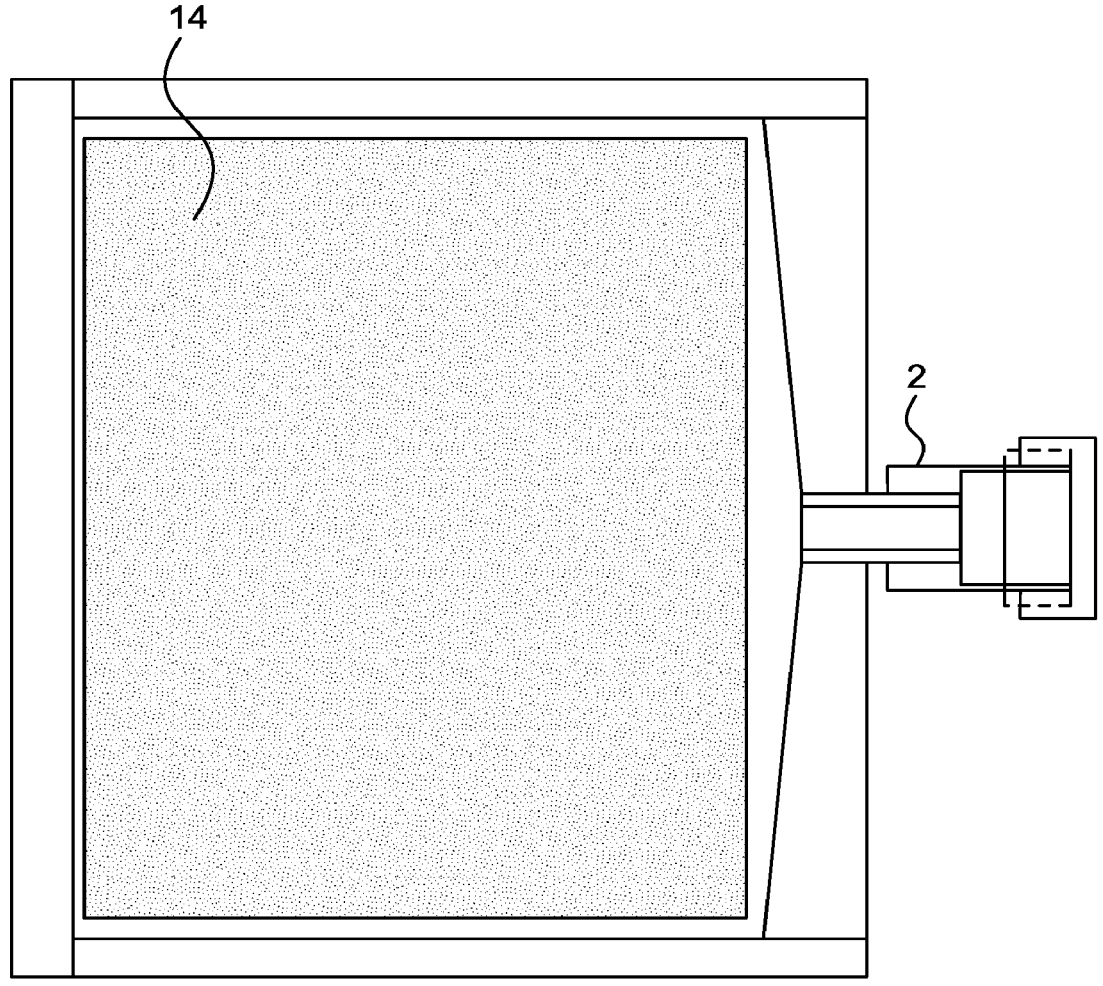
Figures 4A, 4B:
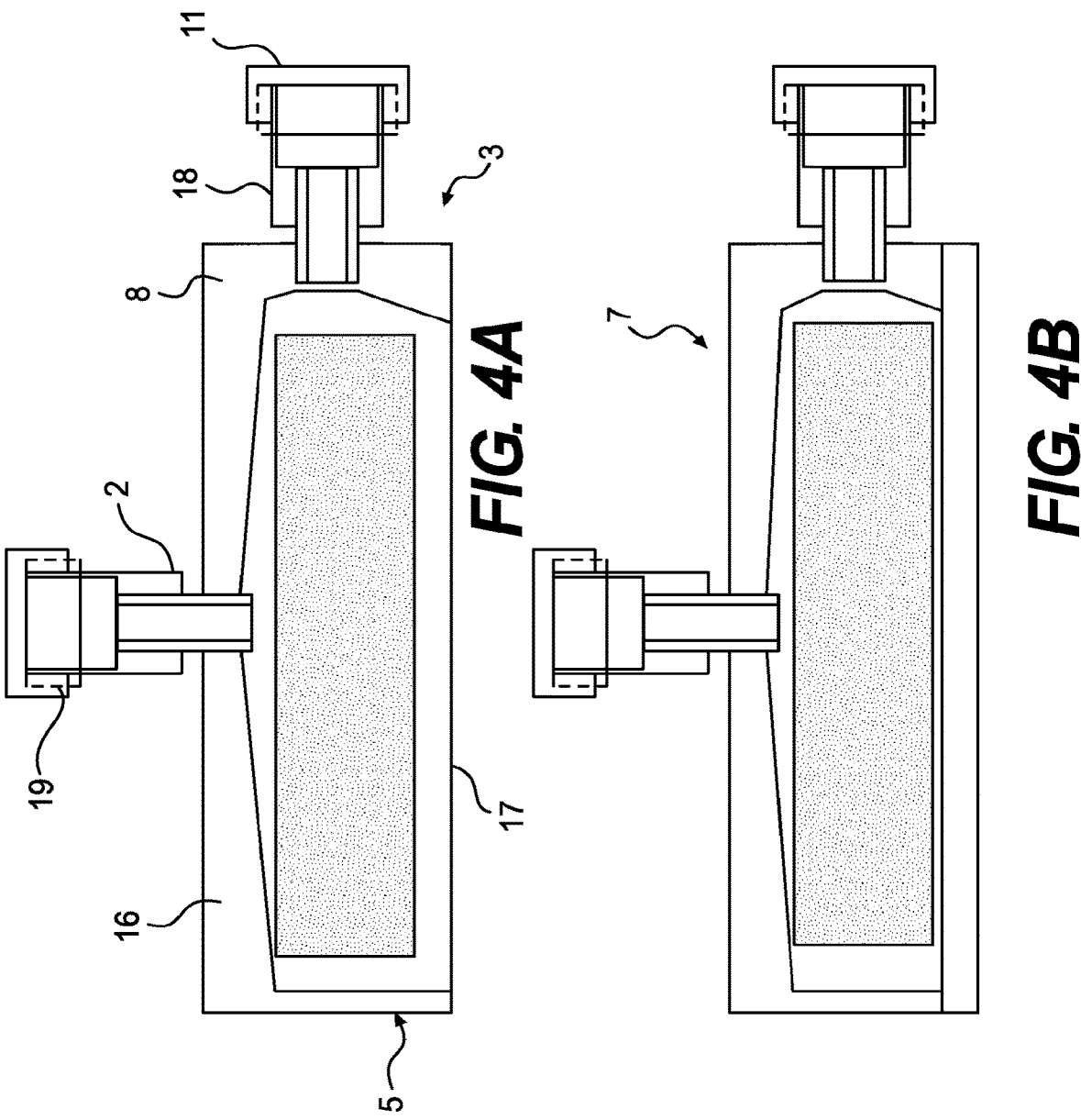
FIGS. 4A-4D present top views of a pouch that includes two ports.
Figures 4C, 4D:
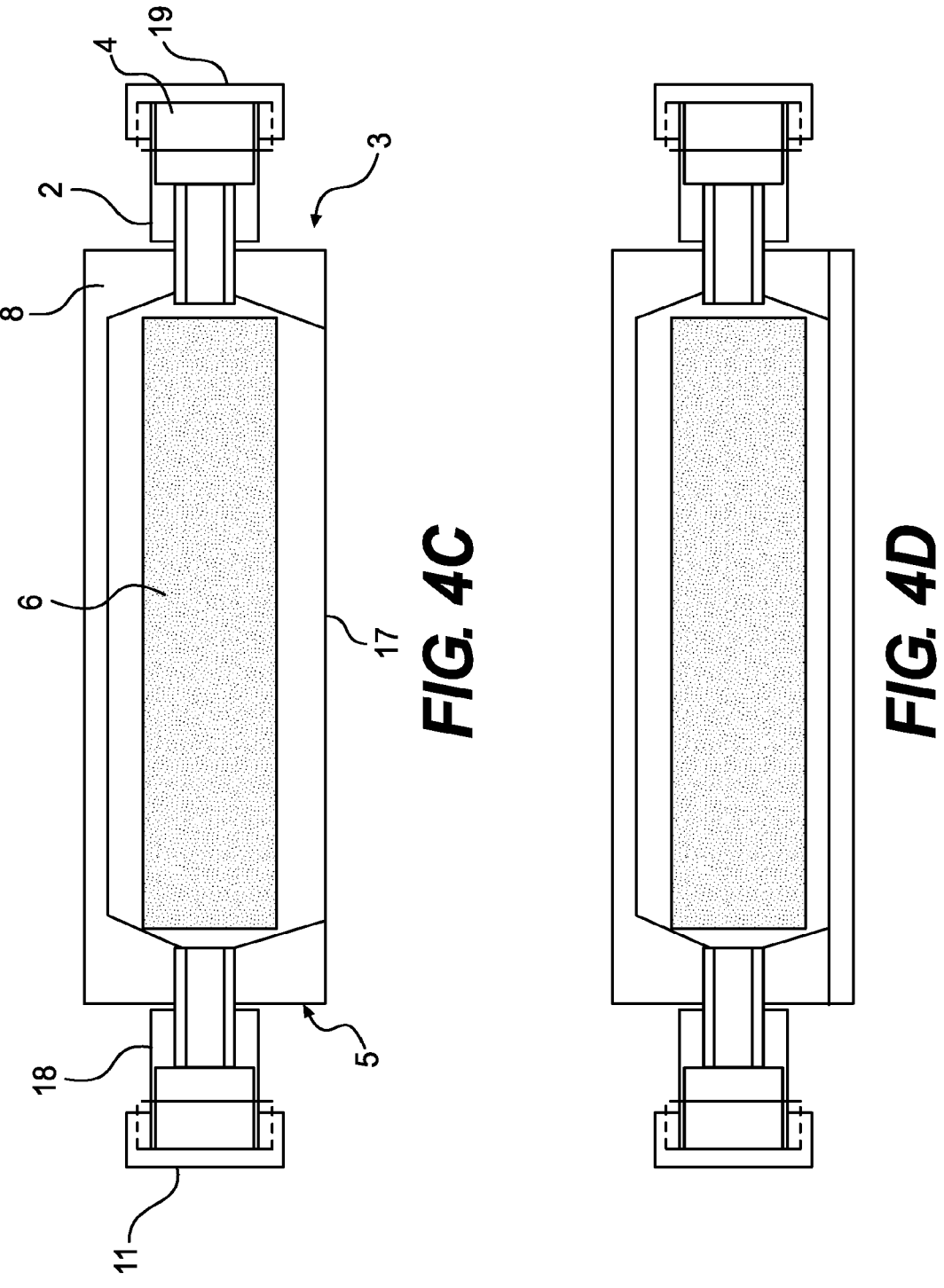

FIGS. 3A and 3B provide views of a large flexible pouch (13) which is bonded and sealed with a needle-free swabable connector (2) at one end (3) and is open at the other end (5). The opening at end (3) on the flexible pouch (13) may be sealed at an angle of about 5 degrees to about 60 degrees (8) from the end of the connector to avoid the dead space that could trap cells or tissues.

One or more sheets of tissue, membrane, or sponge (14) with or without cells may be loaded into the pouch using the opening at end (5). After the tissue and/or cellular material are loaded, additional biological fluids, such as preservation solutions or biological solutions, may be added from either end of the pouch. The opening at end (5) then may be sealed.

Cellular material and/or biological fluids may also be loaded from the needle-free swabable connector (2). If the cellular material and/or biological fluids will be loaded from the needle-free swabable connector (2), the opening (5) will be sealed first, then the fluids or cells will be injected in through the needle-free swabable connector (2). The sealed package (15) containing tissue and/or cellular material will be placed in a secondary container and sealed again to prevent contamination.

The flexible pouch (13) may be made from a tube (FIG. 3A) or made from two sheets of films (FIG. 3B) that are bonded together.

As with certain embodiments of the invention, including, but not limited to, those shown in FIGS. 1A, 1B, 2A, 2B, 3A and 3B, the designed thickness of the wall of the flexible pouch (13) advantageously facilitates efficient heat/cold transfer and controlled freezing. In addition, during thawing of the cryopreserved tissue and/or cells, the designed thickness of the wall allows quick thaw of the tissue and/or cells, which is useful for maintaining cell viability.

FIGS. 4A-4D present other embodiments of the present invention featuring a pouch with at least two ports. One port may be used to pump cryopreservation media into the pouch, and another port may be used for removing and washing the contents. The two port design may be used to prevent potential cross contamination of the pouch and its contents. The two port design may also be used to inject biological fluids into the pouch and facilitate mixing by moving two syringes back and forth.

A flexible pouch (16) may be bonded and sealed with at least two needle-free swabable connectors (2) in two of the four openings. One of the remaining two openings may be sealed, leaving one opening on the side along the long axis (17). The openings that are bonded and sealed with the connectors (2) on the flexible pouch (16) may be sealed at an angle of about 5 degrees to about 60 degrees (8) to avoid the dead space that could trap cellular material and/or tissue.

The connectors (2) may be connected to a luer lock adaptor or connector without using any needle. For example, one of the connectors (2) may be used to fill in cellular material and/or biological solutions or preservation solution during processing. The other connector (18) may be used to remove the filled solutions during processing, and may be used for rinsing or injecting biological fluid right before applied to the patients.

In one aspect, tissue and/or cellular material (6) may be loaded into the pouch from the opening on the side along the long axis (17) and then the opening (17) may be sealed.

During processing, cellular material and/or biological fluids may be loaded from one of the needle-free swabable connectors (2) or (18). In the case that cellular material and/or biological fluids will be loaded from the needle-free swabable connector (2), all openings will be sealed prior to loading. In one aspect, connector (18) is designed to remain clean and unused until application of the tissue and/or cellular material to patients. Connector (18) may be capped with a clear color cap (11). Biological fluids and/or cellular material then may be injected through the needle-free swabable connector (2) and capped with a cap (19). The sealed package (7) containing tissue and/or cellular material may be placed in a secondary container and sealed again to prevent contamination.

For cryopreserved tissue, the sealed package in a secondary container may be frozen at a controlled freezing rate to about −70° C. or lower, placed in a box, and stored in vapor phase liquid nitrogen. Prior to application of the tissue and/or cellular material, the package may be placed in a sterile container with 35-39° C. sterile isotonic solutions to quickly thaw the cellular material/tissue. At this point, the clear cap (11) may be removed and the preservation media or cellular material may be discharged from the pouch through the connector (18). Optionally, the tissue/cellular material may be rinsed or combined with biological solutions through the connector (18). The sealed opening (17) may be cut open to allow access to the tissue/cellular material.

Figures 5A, 5B, 5C:
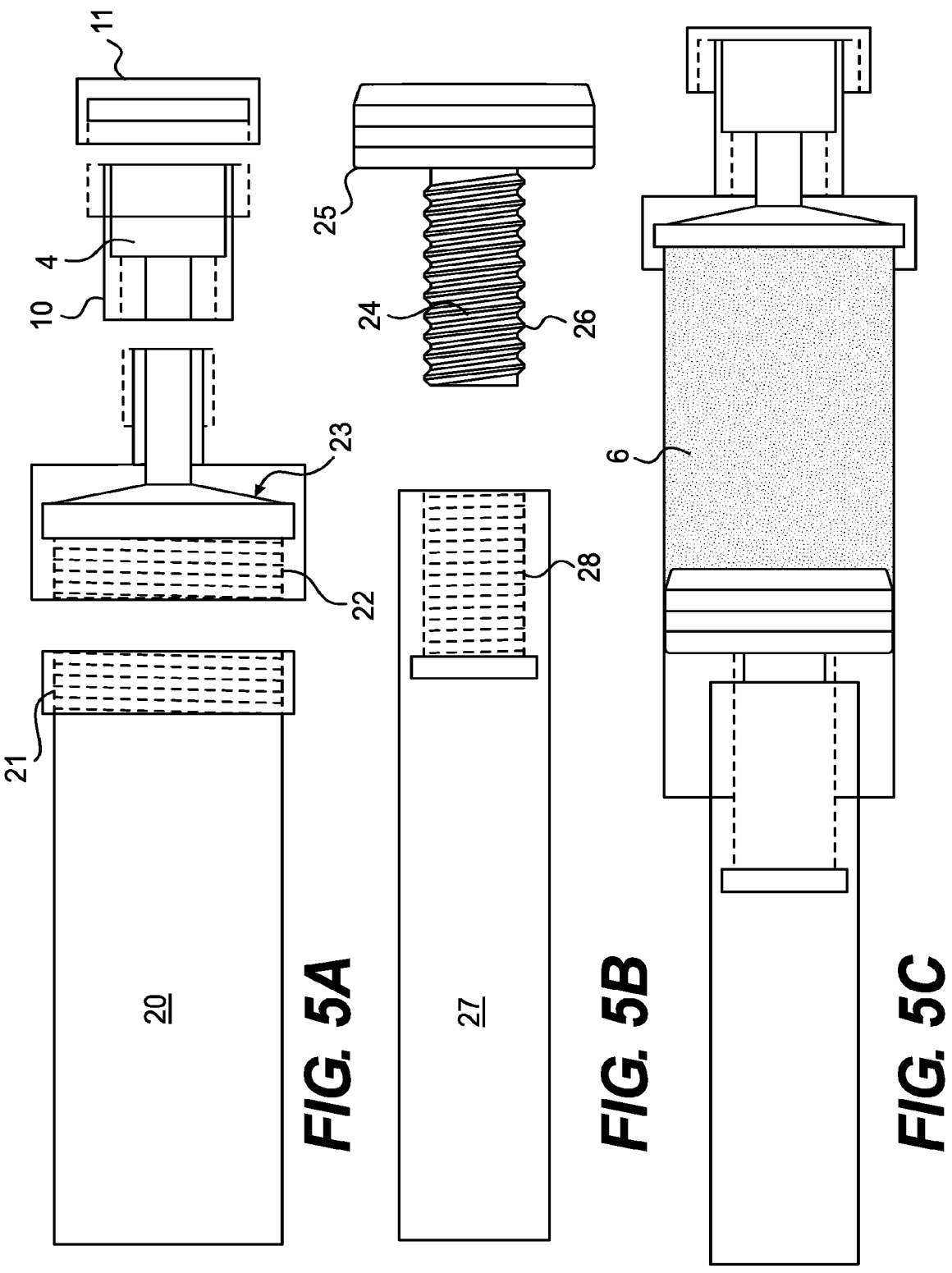
FIGS. 5A-5C present top views of a rigid tube designed to contain tissue and/or cellular material. The tube is connected to a threaded adaptor in one end and may be fitted with a handle connected to a plunger in another end, which in turn may be used to discharge the contents.

In another embodiment of the invention, FIGS. 5A-5C show a rigid cylindrical tube (20) made from biocompatible materials with a threaded end (21) which is connected to a threaded adaptor (22) through a female threaded end. The male threaded end of the threaded adaptor (22) may be connected to a needle-free swabable connector (10) that is capped with a cap (11). A conical portion (23) within in the threaded adaptor (22) may be included and is designed to avoid the dead space that could trap cellular material or tissues.

After the rigid cylindrical tube (20) is connected to the threaded adaptor (22), tissue and/or cellular material (6) may be loaded into the tube from an unthreaded opening of the rigid cylindrical tube (20). In certain aspects, a plunger (23) with a conical shape plunger head (25) may be pushed into the rigid tube (20). The plunger head (25), which may be made of silicon or thermoplastic elastomer, provides a seal. The plunger (24) may also have a male threaded end (26) or include other structures to provide a seal.

For cryopreserved tissue, the sealed package in a secondary container may be frozen at a controlled freezing rate to about −70° C. or lower, placed in a box, and stored in vapor phase liquid nitrogen. Before the tissue and/or cellular material are applied, the package may be placed in a sterile container with 35-39° C. sterile isotonic solutions to thaw the contents. The cap (11) may be removed and the preservation media or cellular material may be discharged through the connector (10). Optionally, the tissue/cellular material may be rinsed or combined with biological solutions through the connector (10). A handle (27), optionally provided in a kit, may be threaded onto the plunger's (24) male threaded end (26) through its female threaded end (28). The threaded adaptor (22) may be removed and the entire contents within the rigid tube (20) may be pushed out by the plunger (24) and handle (27) assembly.

Figure 6:
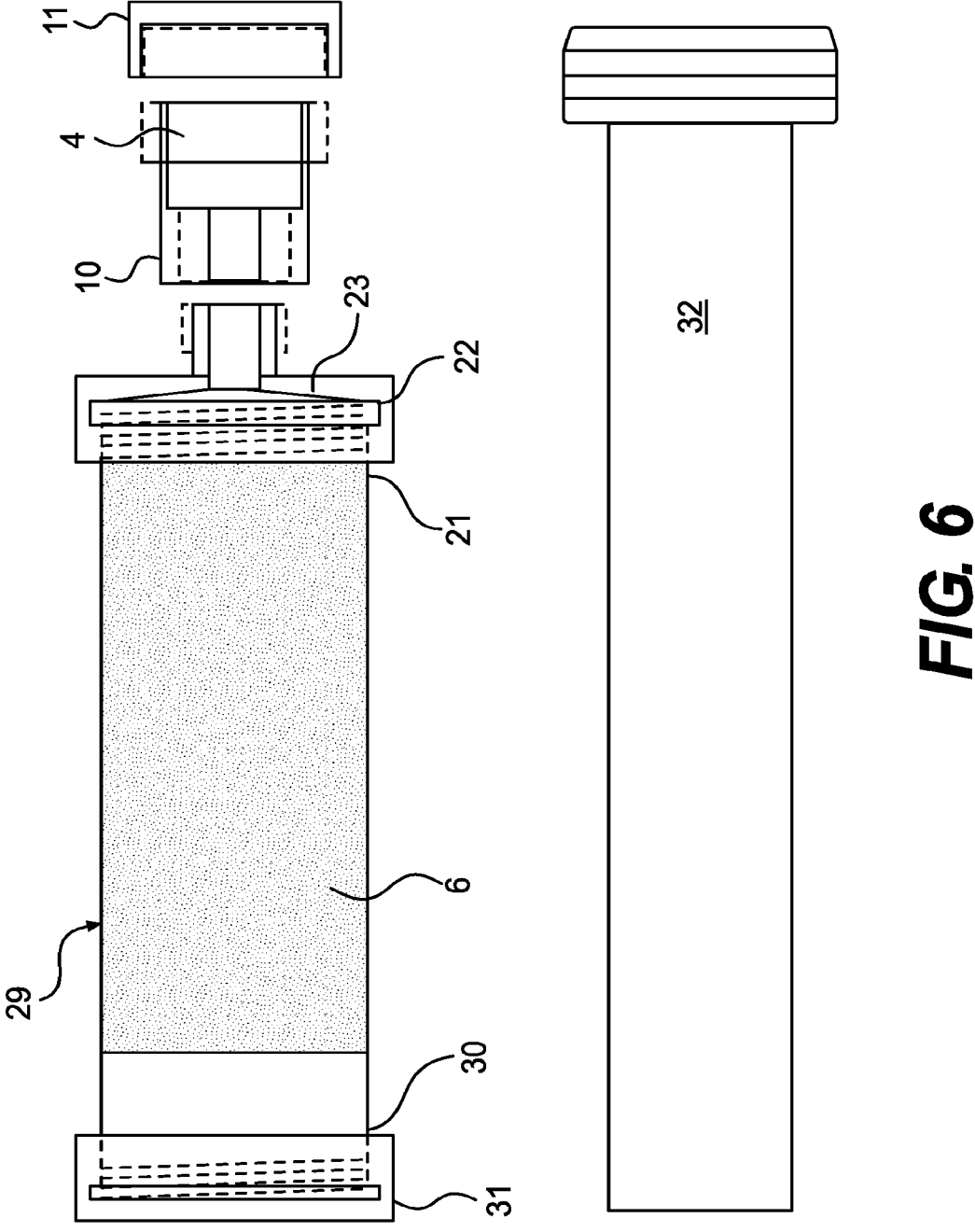
FIG. 6 presents top views of a rigid tube which may be used in combination with a plunger and a swabable connector.

FIG. 6 shows another embodiment of the invention which includes a plunger that may be used to push tissue and/or cellular material from the tube or pouch. A rigid cylindrical tube (29) made from biocompatible materials with two male threaded ends (21) and (30) is connected to a threaded adaptor (22) through one of the male threaded ends. The male threaded end of the threaded adaptor (22) is connected to a needle-free swabable connector (10) that is capped with a cap (11). A conical portion (23) within in the threaded adaptor (22) may be included, which is designed to avoid the dead space that could trap cellular material or tissues.

The connectors (10) may be attached to a luer lock connector or adaptor without using any needle. One of the connectors (10) may be used to add cellular material and/or biological solutions or preservation solution during processing.

The valve (4) within the connector (10) may be made, e.g., of silicon or thermoplastic elastomer and is designed to provide the seal to prevent fluid leaking from the packaging. In one aspect, a luer lock connector is connected to the needle-free swabable connector, which permits the valve to be opened and allows fluid to be exchanged freely. The sealed valve may be used to create a vacuum environment in the tube if desired.

Should the rigid cylindrical tube (29) be connected to the threaded adaptor (22), tissue and/or cellular material (6) may be loaded into the tube from the second threaded opening (30) of the rigid cylindrical tube (29). A threaded cap (31) may be secured in place to seal the threaded end (30).

For cryopreserved tissue, the sealed package in a secondary container will be frozen at a controlled freezing rate to about −70° C. or lower, placed in a box, and stored in vapor phase liquid nitrogen. Prior to and, typically, immediately before implantation of the tissue and/or cellular material, the package may be placed in a sterile container with 35-39° C. sterile isotonic solutions to thaw the cellular material/tissue. At this point, the cap (11) may be removed and the preservation media or cellular material may be discharged through the connector (10). Optionally, the tissue/cellular material may be rinsed or combined with biological solutions through the connector (10). Also, optionally, the tissue/cellular material may be incubated with the biological solution for a certain period of time before application. The threaded cap (31) may be removed and a plunger (32) may be fit into the rigid tube (29). Plunger (32) may be provided as part of the kit. Threaded adaptor (22) may be removed, and the entire contents within the rigid tube (29) may be pushed out by the plunger (32).

Figures 7A, 7B:
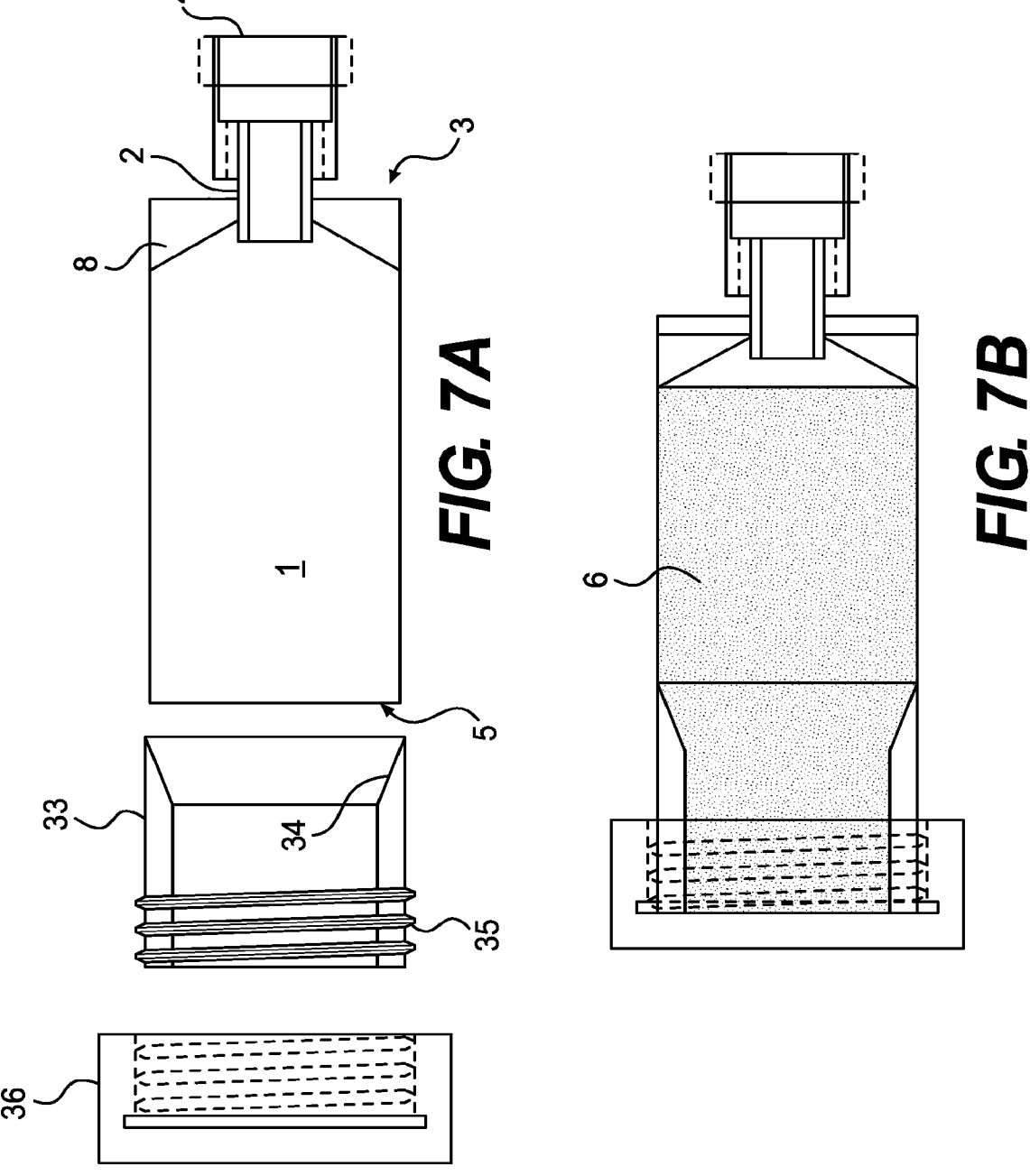
FIGS. 7A and 7B present top views of a flexible pouch which is bonded to a rigid tube. The flexible tube includes a swabable connector with a valve.

In the embodiment shown in FIGS. 7A and 7B, a flexible pouch (1) made from biocompatible materials is bonded and sealed with a needle-free swabable connector (2) in one end (3) and is open at the other end (5). The opening (3) on the flexible pouch (1) is sealed at an angle of from about 5 degrees to about 60 degrees (8) to avoid the dead space that could trap cellular material or tissues. A rigid tube (33) that has a beveled edge in one end (34) and a male thread on the other end (35) is bonded and sealed with the flexible pouch (1). The rigid tube may be made from biocompatible materials.

Tissue and/or cellular material (6) may be loaded into the pouch through the rigid tube (33) that is bonded and sealed with the pouch (1). After the tissue and/or cellular material are loaded, additional biological fluids, such as preservation media may be added from either end. The rigid tube (33) may be sealed with a female threaded cap (36).

Cellular material and/or biological fluids also may be loaded from the needle-free swabable connector (2). If the cellular material and/or biological fluids are loaded from the needle-free swabable connector (2), the rigid tube (33) may be sealed first, then the fluids or cellular material may be injected into the package through the needle-free swabable connector (2). The sealed package containing tissue and/or cellular material may be placed in a secondary container and sealed again to prevent contamination.

Figures 8A, 8B:
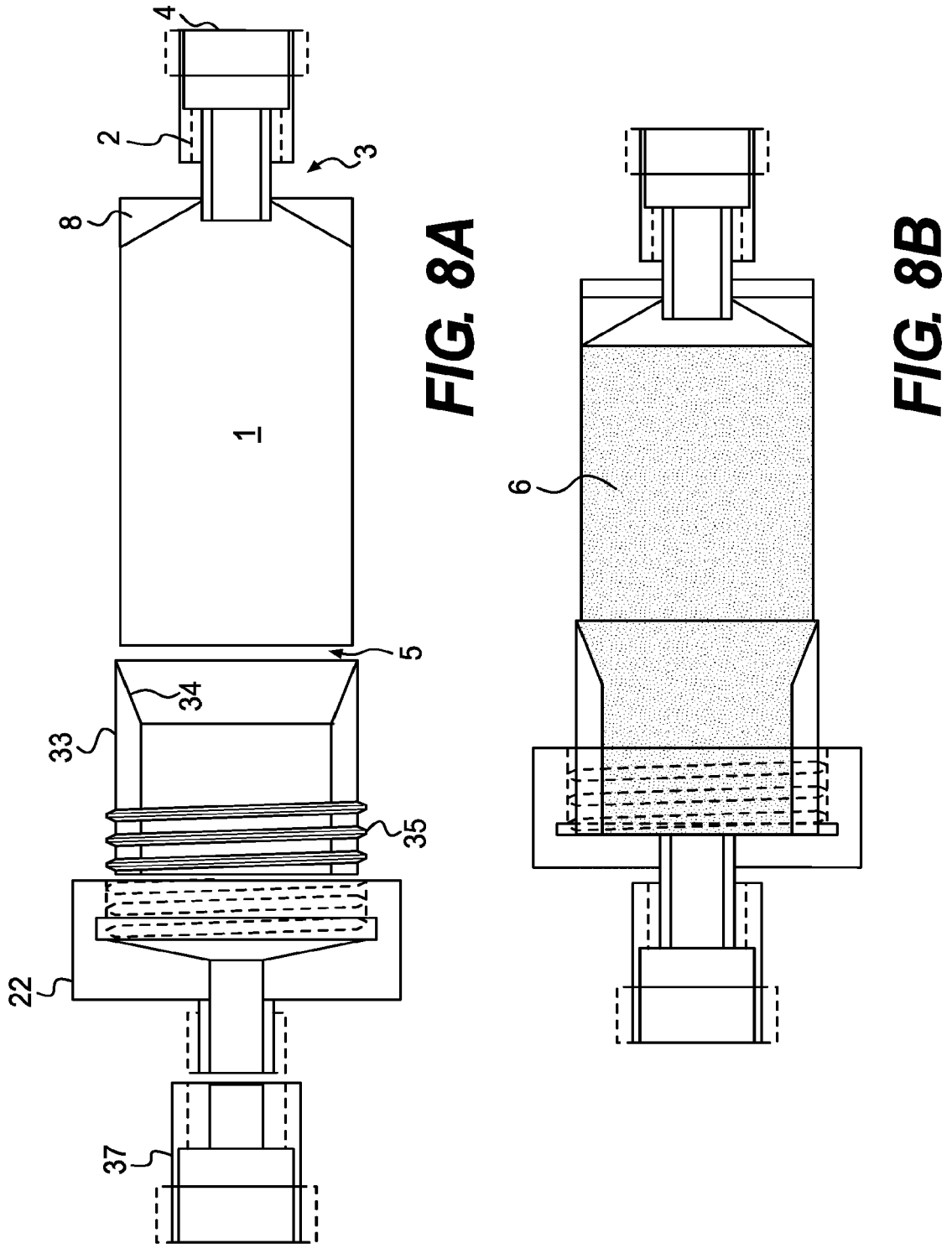
FIGS. 8A and 8B present top views of a flexible pouch which is bonded to a rigid tube that is connected to a threaded adaptor. Both the flexible tube and the threaded adaptor are fitted with swabable connectors.

FIGS. 8A and 8B provide another embodiment of the invention in which a rigid tube may be bonded to a flexible tube or pouch. A flexible pouch (1) made from biocompatible materials is bonded and sealed with a needle-free swabable connector (2) in one end (3) and is open at the other end (5). The opening (3) on the flexible pouch (1) is sealed at an angle of about 5 degrees to about 60 degrees (8) to avoid the dead space that could trap cellular material or tissues. A rigid tube (33) that has a beveled edge in one end (34) and a male thread on the other end (35) is bonded and sealed with the flexible pouch (1). The rigid tube may be made from biocompatible materials.

Tissue and/or cellular material (6) may be loaded into the pouch through the rigid tube (33) that is bonded and sealed to the pouch (1). After the tissue and/or cellular material are loaded, additional biological fluids, such as preservation media may be added from either end. The rigid tube (33) may be connected to the threaded adaptor (22) and sealed with a needle-free swabable connector (37).

Cellular material and/or biological fluids also may be loaded from the needle-free swabable connector (2). If the cellular material and/or biological fluids are loaded from the needle-free swabable connector (2), the rigid tube (33) along with the threaded adaptor (22) may be sealed first with a needle-free swabable connector (37), at which point the fluids or cellular material may be injected through the needle-free swabable connector (2). The sealed package containing tissue and/or cellular material may be placed in a secondary container and sealed again to prevent contamination.

For cryopreserved tissue, the sealed package in a secondary container may be frozen at a controlled freezing rate to about −70° C. or lower, placed in a box, and stored in vapor phase liquid nitrogen. Just before it is applied, the tissue and/or cellular material, the package may be placed in a sterile container with 35-39° C. sterile isotonic solutions to thaw the tissue and/or cellular material quickly. At this point, the preservation media or cellular material may be removed through the connector (2) or (37). Optionally, the tissue/cellular material may be rinsed or combined with biological solutions through the connector (2) or (37) and fully mixed within the pouch using two syringes that are connected to connectors (2) and (37) to push back and forth. The threaded adaptor (22) then may be removed to allow access to the tissue/cellular material.

Figures 9A, 9B:
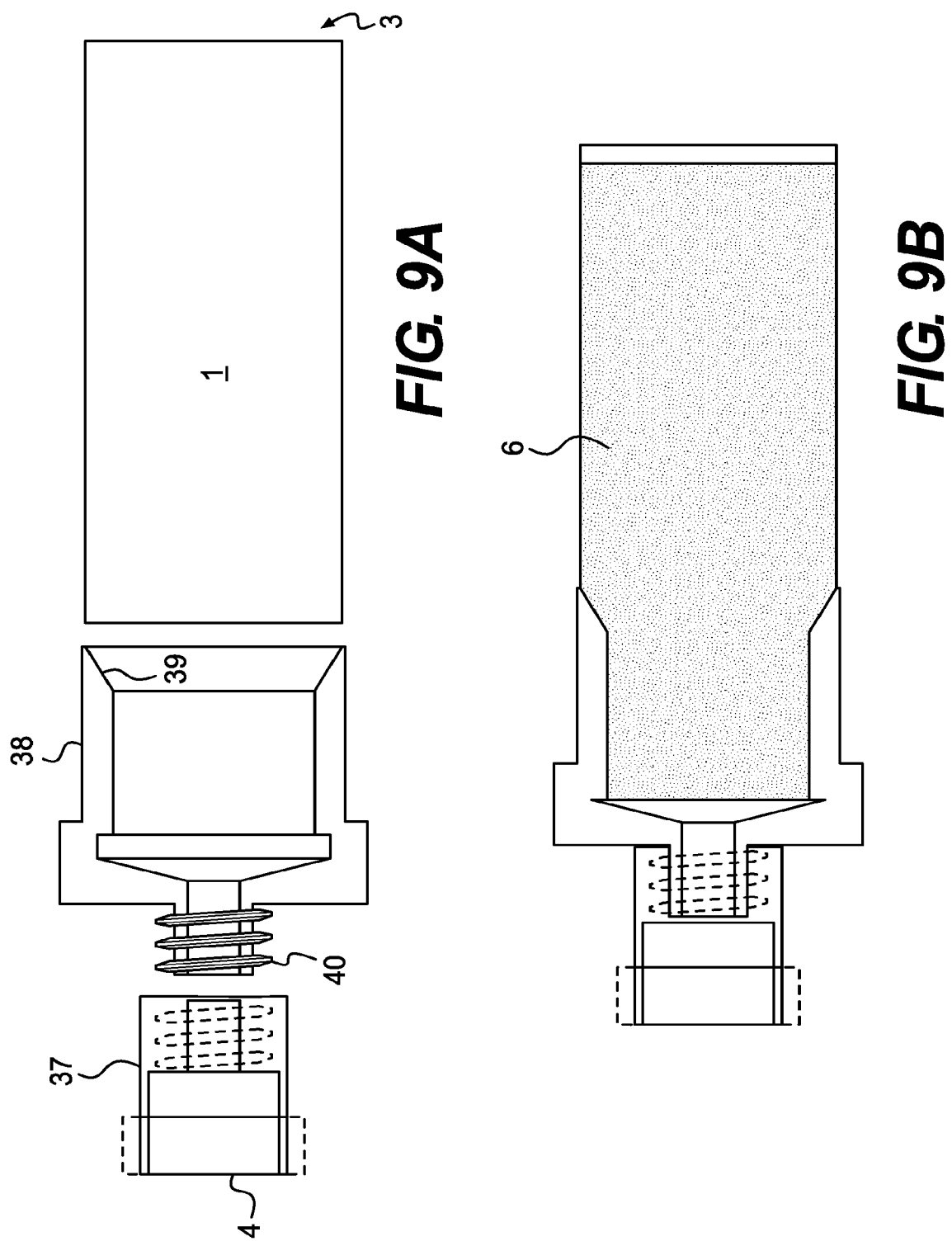
FIGS. 9A and 9B present top views of a flexible pouch which is bonded to a rigid tube. In this embodiment, only the rigid tube is fitted with a swabable connector.

FIGS. 9A and 9B provide another embodiment of the invention in which a rigid tube may be bonded to a flexible tube or pouch. A flexible pouch (1) made of biocompatible materials is bonded and sealed with a rigid threaded tube (38) that has a beveled edge in one end (39) and a male thread on the other end (40). The rigid tube is made from biocompatible materials. The threaded end (40) of the tube (38) may be connected to a needle-free swabable connector (37) to seal the opening. The other opening of the pouch (3) remains open until tissue and/or cellular material are loaded into the pouch.

The valve (4) within the connector (37), which may be made of silicon or thermoplastic elastomer, provides the seal to prevent fluid leaking from the packaging. Only when a luer lock connector is attached to the needle-free swabable connector, will the valve be opened and allow fluid to be exchanged freely. The sealed valve may be used to create a vacuum environment in the pouch if desired.

Tissue and/or cellular material (6) will be loaded into the pouch through the opening (3). After the tissue and/or cellular material are loaded, additional biological fluids, such as preservation solution may be added from either end. The opening (3) then may be sealed.

Cellular material and/or biological fluids also may be loaded from the needle-free swabable connector (37). If the cellular material and/or biological fluids will be loaded from the needle-free swabable connector (37), the opening (3) may be sealed first, then the fluids or cellular material may be injected in through the needle-free swabable connector (37). The sealed package containing tissue and/or cellular material may be placed in a secondary container and sealed again to prevent contamination.

For cryopreserved tissue, the sealed package in a secondary container may be frozen at a controlled freezing rate to about −70° C. or lower, placed in a box, and stored in vapor phase liquid nitrogen. Just before the tissue and/or cellular material is applied, the package will be placed in a sterile container with 35-39° C. sterile isotonic solutions to thaw the tissue and/or cellular material quickly. At this point, the preservation media or cellular material may be removed through the connector (37). Optionally, the tissue/cellular material may be rinsed or combined with biological solutions through the connector (37). The sealed end (3) may be cut open to allow access to the tissue/cellular material.

Figure 10:
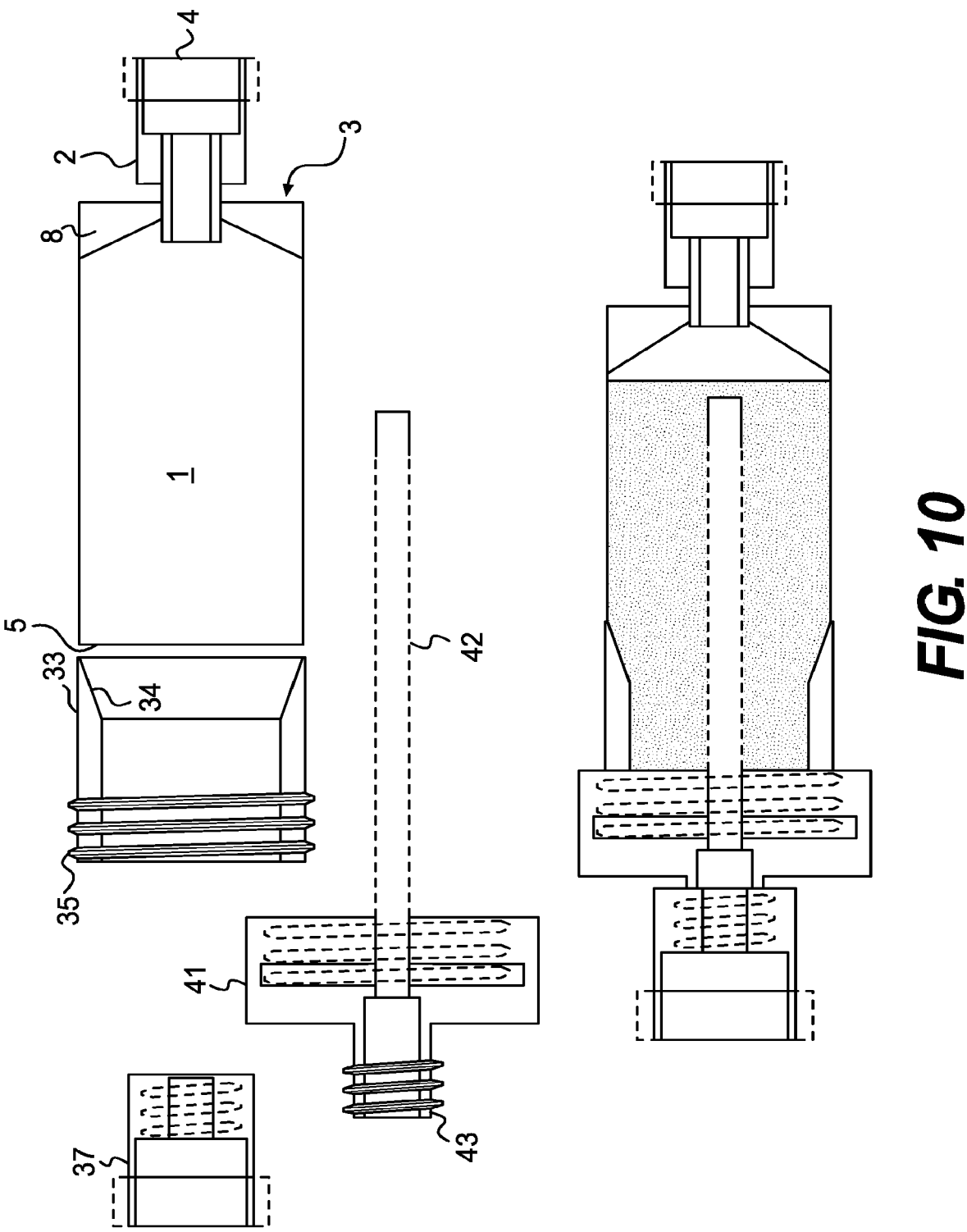
FIG. 10 presents a top view of a flexible pouch which is bonded to a rigid tube. In this embodiment the rigid tube is adapted for engagement with a needle having side channels, which may be used to inject biological fluid or solution to distribute it evenly through the length of the pouch.

In FIG. 10 a flexible pouch (1) made from biocompatible materials is bonded and sealed with a needle-free swabable connector (2) in one end (3) and open at the other end (5). The opening (3) on the flexible pouch (1) is sealed at an angle of 5 degrees to 60 degrees (8) to avoid the dead space that could trap tissue and/or cellular material. A rigid tube (33) that has a beveled edge in one end (34) and a male thread on the other end (35) is bonded and sealed with the flexible pouch (1). The rigid tube may be made from biocompatible materials.

Tissue and/or cellular material (6) may be loaded into the pouch through the rigid tube (33) that is bonded and sealed with the pouch (1). After the tissue and/or cellular material are loaded, additional biological fluids such as preservation solution may be added from either end. The rigid tube (33) may be connected to a threaded adaptor (41) that has a needle with side channels (42) and a male threaded end (43). The length of the needle may extend the entire length of the flexible pouch (1). The needle (42) may be embedded in the tissue and/or cellular material. The swabable connector (37) then may be connected to the threaded end (43) of the threaded adaptor (41) to provide a seal.

Cellular material and/or biological fluids may also be loaded from the needle-free swabable connector (2). If the cellular material and/or biological fluids are loaded from the needle-free swabable connector (2), the rigid tube (33) along with the threaded adaptor (41) may be sealed first, then the fluids or cellular material may be injected through the needle-free swabable connector (2). The sealed package containing tissue and/or cellular material may be placed in a secondary container and sealed again to prevent contamination.

For cryopreserved tissue, the sealed package in a secondary container may be frozen at a controlled freezing rate to about −70° C. or lower, placed in a box, and stored in vapor phase liquid nitrogen. Right before the tissue and/or cellular material are applied, the package may be placed in a sterile container with 35-39° C. sterile isotonic solutions to thaw the tissue and/or cellular material quickly. Then the preservation media or cellular material may be removed through the connector (2). Optionally, the tissue and/or cellular material may be rinsed or combined with biological solutions through the connector (37). In order to efficiently distribute the biological solutions in the tissue and/or cellular material along the length of the pouch (1), a vacuum environment may be created by removing all air from either connector (2) or (37). At this point, biological fluid may be injected through connector (37) and the fluid will be distributed through the side channels of the needle (42) along the length of the pouch. Due to the flexibility of the pouch (1), the tissue and/or cellular material and the biological fluid may be massaged to facilitate the mixing process. The threaded adaptor (41) then may be removed to allow access to the tissue/cellular material. Alternatively, the pouch end sealed with the connector (2) may be cut open to allow access to the tissue.

Figure 11:
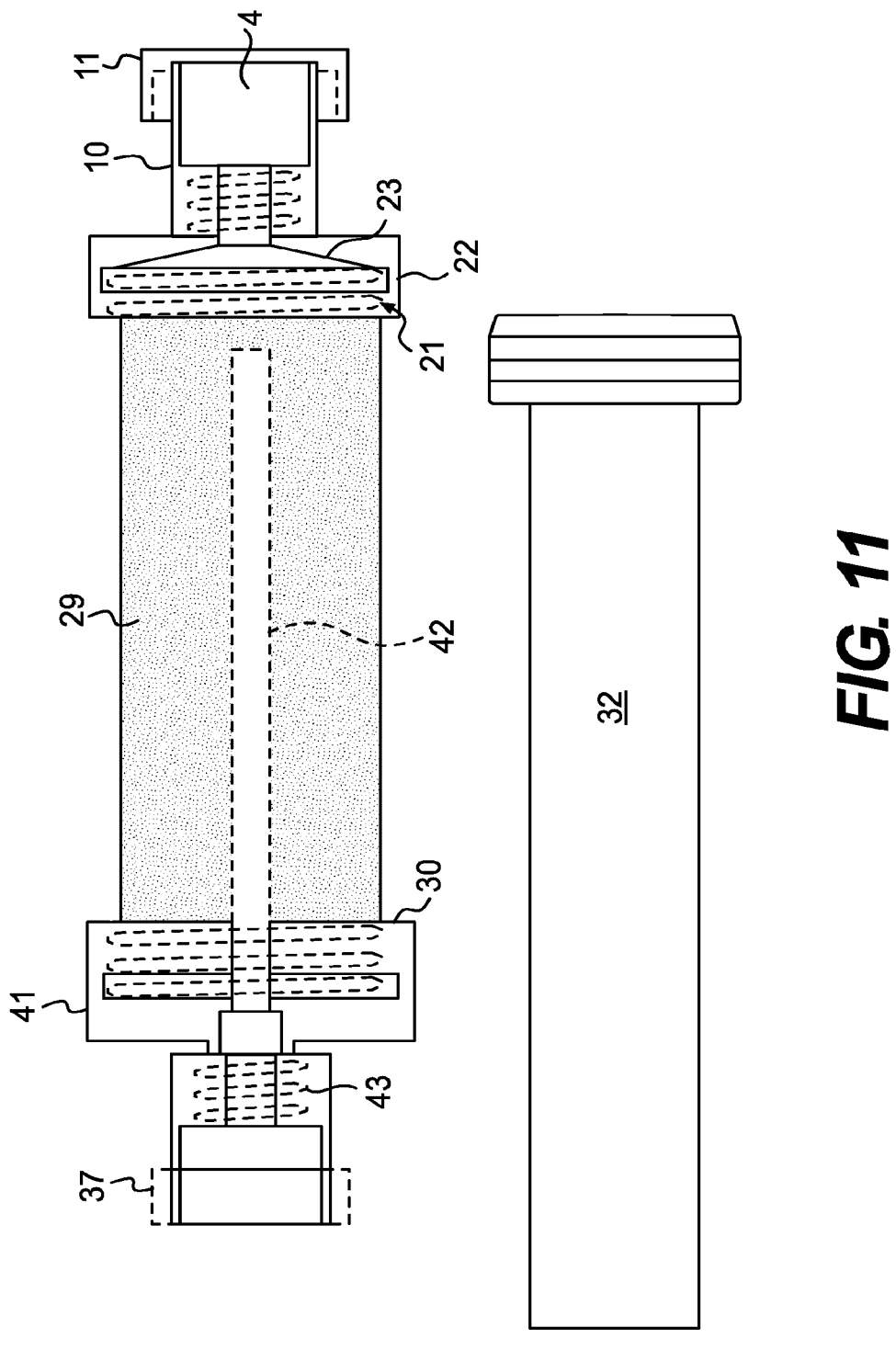
FIG. 11 presents a top view of a rigid tube, which includes the presence of a needle with side channels, and is also adapted for use of a plunger to discharge tissue and/or cellular material.

In FIG. 11, a rigid cylindrical tube (29) made from biocompatible materials with two threaded ends (21) and (30) may be connected to a threaded adaptor (22) through the threaded end (21). The male threaded end of the threaded adaptor (22) may be connected to a needle-free swabable connector (10) that may be closed with a cap (11). A conical portion (23) within in the threaded adaptor (22) is designed to avoid the dead space that could trap cellular material or tissues.

After the rigid cylindrical tube (29) is connected to the threaded adaptor (22), tissue and/or cellular material (6) may be loaded into the tube from the second threaded opening (30) of the rigid cylindrical tube (29). After the tissue and/or cellular material are loaded, additional biological fluids, such as preservation media, may be added from either end. The rigid tube (29) may be connected to the threaded adaptor (41) that may include a needle with side channels (42) and a male threaded end (43). The length of the needle may extend the entire length of the rigid tube (29). The needle (42) may be embedded in the tissue and/or cellular material. The swabable connector (37) then may be connected to the threaded end (43) of the threaded adaptor (41) to provide a seal.

The needle (42) may extend the entire length of the pouch and be embedded in the loaded material in the pouch. In one embodiment, the end of the needle is sealed so that the fluid may only flow through the side channels. Alternatively, the end of the needle may have a blunt end and be kept open so that the fluid may flow through from both the side channels and the end. The inner diameter of the needle may be from about 0.5 mm to about 5 mm. In one embodiment of the invention, the inner diameter of the needle is from about 1 mm to about 4 mm. The wall thickness of the needle may be from about 0.05 mm to about 0.5 mm. In one embodiment of the invention, the wall thickness of the needle is from about 0.1 mm to about 0.4 mm. The needle may be made from biocompatible materials. The diameter of the side channels may range from about 0.05 mm to about 4 mm. In one embodiment of the invention, the diameter of the side channels is from about 0.1 mm to about 3 mm. Two to four holes may be evenly distributed around the diameter of the needle to create the side channels.

For cryopreserved tissue, the sealed package in a secondary container may be frozen at a controlled freezing rate to about –70° C. or lower, placed in a box, and stored in vapor phase liquid nitrogen. Right before the tissue and/or cellular material are applied, the package may be placed in a sterile container with 35-39° C. sterile isotonic solutions to thaw the tissue and/or cellular material quickly. The cap (11) then may be removed and the preservation media or cellular material may be removed through the connector (10). Optionally, the tissue and/or cellular material may be rinsed or combined with biological solutions through the connector (37) and/or (10). In order to efficiently distribute the biological solutions in the tissue and/or cellular material along the length of the tube (29), a vacuum environment may be created by removing all air from either connector (10) or (37). The biological fluid then may be injected through connector (37) and the fluid may be distributed through the side channels of the needle (42) along the length of the tube. The biological fluids may also be injected simultaneously through both connectors (10) and (37) to facilitate a chemical reaction. For example, platelet rich plasma (PRP) may be injected through connector (37) and, at the same time, thrombin or batroxobin may be injected through connector (10) to facilitate the gelation of PRP. The threaded adaptors (41) and (22) may then be removed to allow access to the tissue/cellular material. A plunger (32) provided in the kit may be fit into the rigid tube (29). The entire contents within the rigid tube (29) may be pushed out by the plunger (32).

The plunger is configured to provide a seal and function with smooth movement within the rigid tubing. In addition, the plunger may be adapted to sustain large temperature fluctuations during freezing and thawing.

Figure 12:
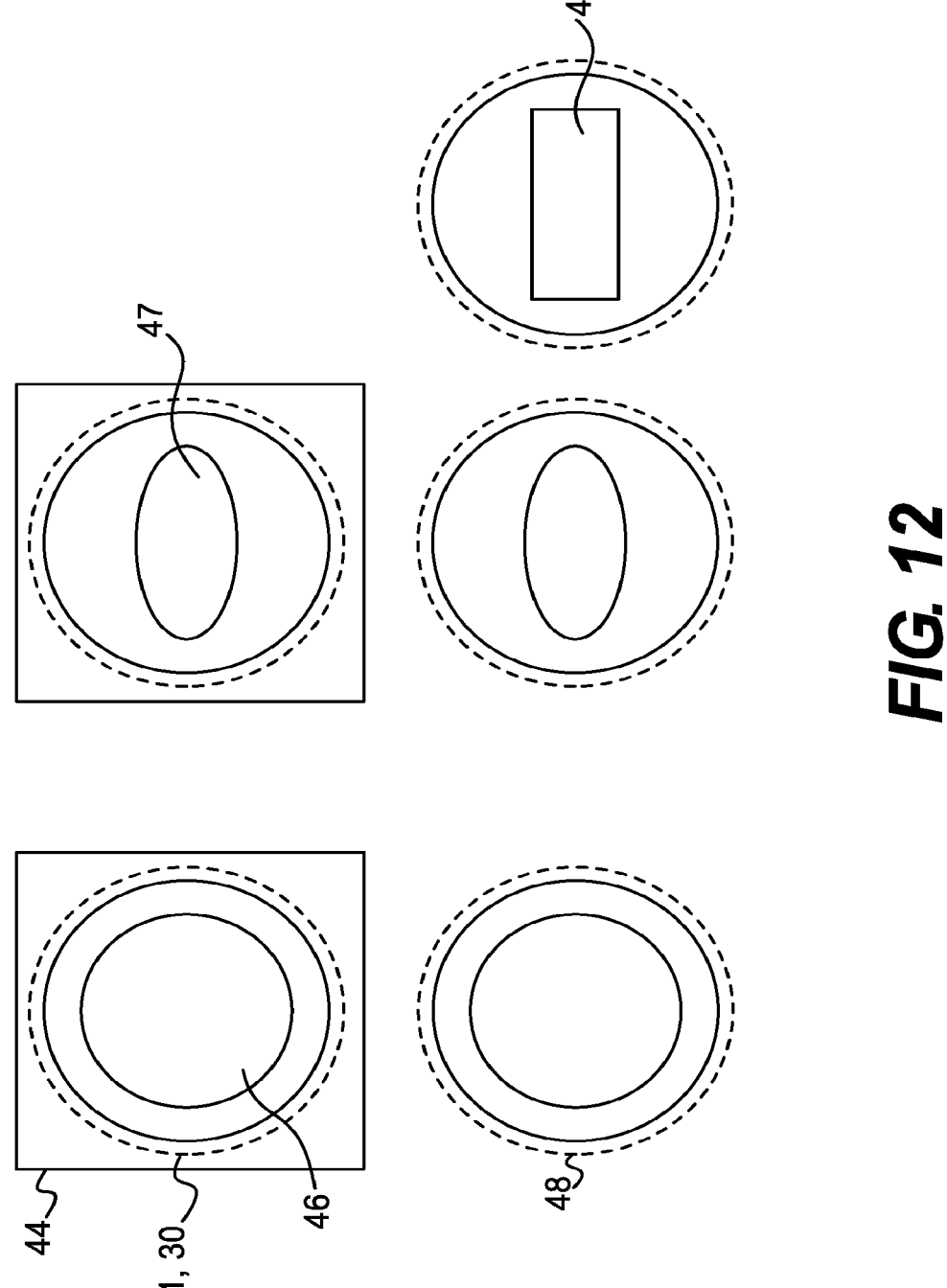
FIG. 12 presents axial views of several embodiments of the present invention.

FIG. 12 provides axial views of various embodiments of the invention. The rigid cylindrical tubes (29) in FIG. 11, with two threaded ends (21) and (30) may have a square or rectangular exterior (44), or a round exterior body (48). The threaded ends (21) and (30) are shown in a round design. The interior of the tube (29) may be a variety of shapes, including round (46), oval shaped (47), rectangular or square (49).

Figure 13A:
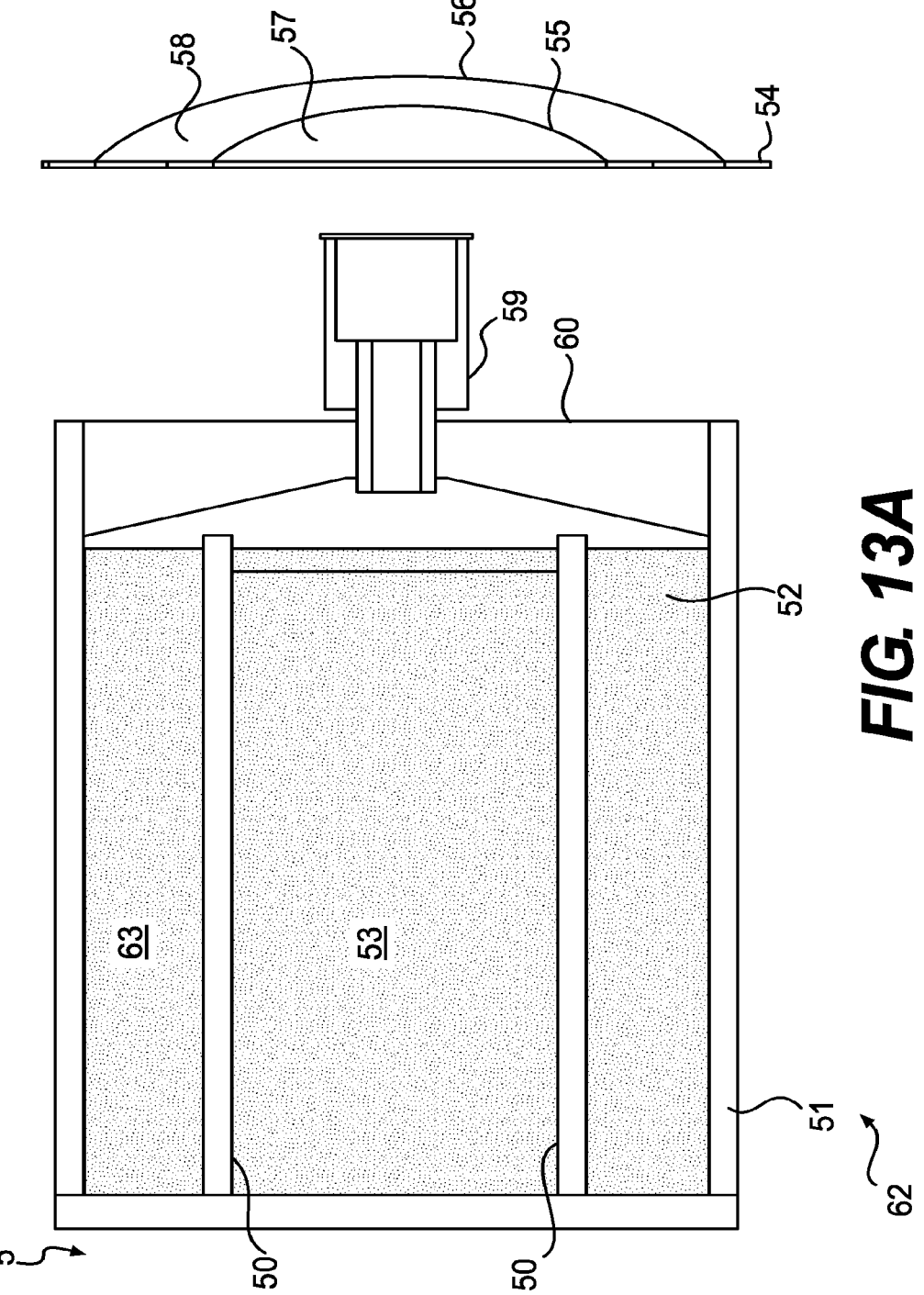
FIGS. 13A and 13B present top views of an embodiment of a large multilayer flexible pouch with multiple compartments. The pouch is bonded and sealed with a needle-free swabable connector at one end.
Figure 13B:
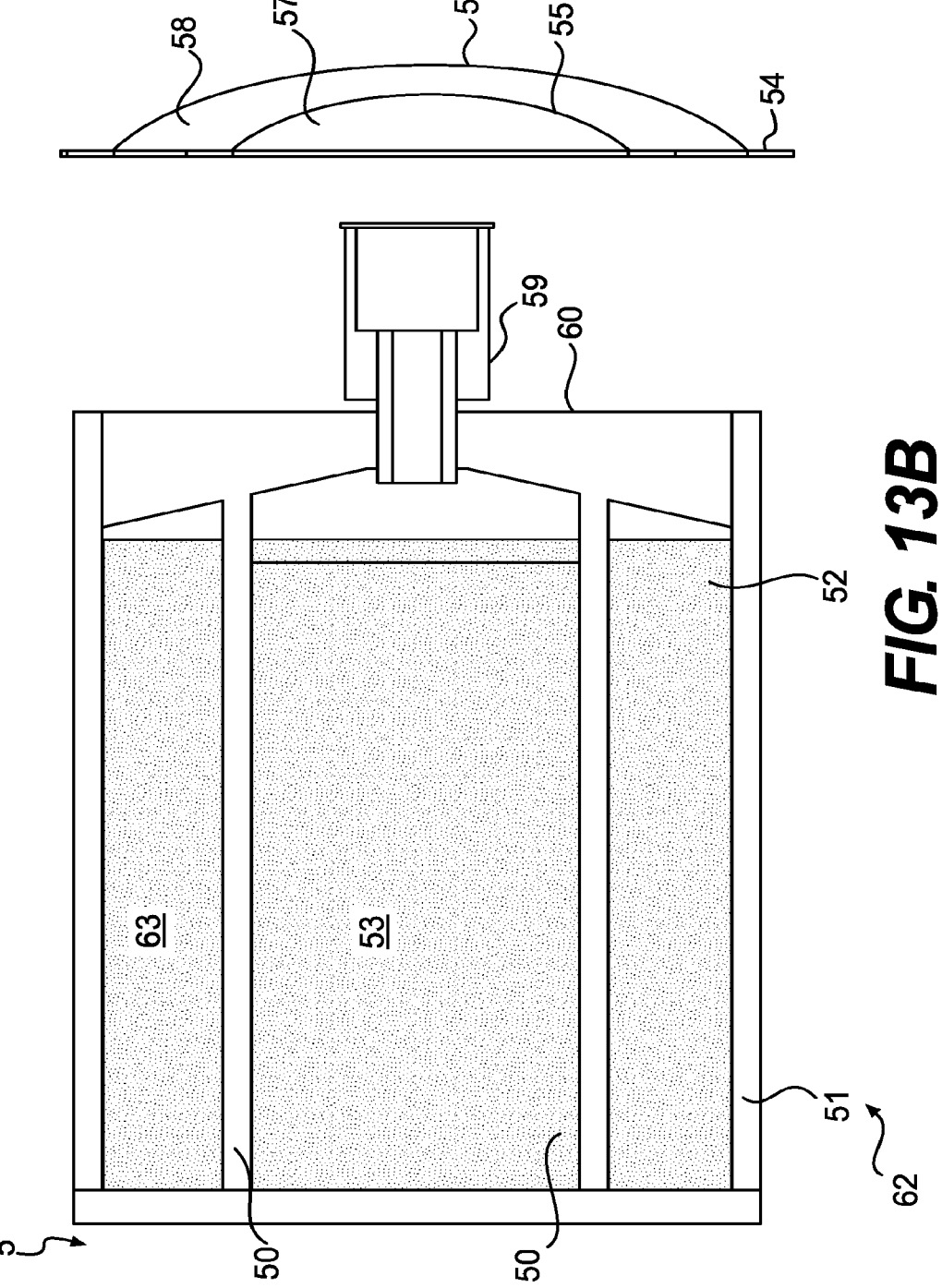

FIG. 13A provides another embodiment of the invention in which a large multilayer flexible pouch (62) is made from bonding and sealing multiple layers of polymeric materials. In this embodiment, Layer 2 (55) of the polymeric material may be bonded and sealed with Layer 1 (54) on two edges (50) to form inner compartment (57). Layer 1 (54) and Layer 3 (56) of the polymeric material may be bonded and sealed at both edges (51) to form an outer compartment (58) which is bonded and sealed with a needle-free swabable connector (59) at one end (60) and is open at the other end (5). The sealed end (60) on the flexible pouch (62) may be sealed at an angle of about 5 degrees to about 60 degrees from the end of the connector to avoid dead space that could trap cells or tissues. In this embodiment, the sealed edges (50) are not extended to the sealed end (60) so that the inner and outer compartments are connected. Alternatively, the sealed edges (50) may be extended to the sealed end (60) as shown in FIG. 13B so that the inner and outer compartments are not connected.

One or more sheets of tissue, membrane, or sponge (53) with or without cells may be loaded into the inner compartment (57) from the opening at end (5). Another sheet of tissue, membrane, or sponge (63) may be loaded into the outer compartment (58). After the tissue and/or cellular material are loaded, additional biological fluids, such as preservation solutions or biological solutions, may be added from either end of the pouch. Both the inner and outer pouch will be sealed through the opening at end (5). Sheet (56) in the outer compartment and sheet (55) in the inner compartment may be the same or different material.

Cellular material and/or biological fluids may also be loaded from the needle-free swabable connector (59). In the case where the cellular material and/or biological fluids are loaded from the needle-free swabable connector (59), the opening at end (5) may be sealed first, at which time the fluids or cellular material may be injected into the pouch through the needle-free swabable connector (59). The sealed package (62) containing tissue and/or cellular material may be placed in a secondary container and sealed again to prevent contamination.

In certain embodiments of the invention, the wall of the flexible pouch is advantageously designed to faciliate efficient heat/cold transfer and controlled freezing. In addition, the designed wall thickness of the pouch is adapted to allow for quick thawing of the cryopreserved tissue and/or cellular material, which is useful for maintaining cell viability.

Figure 14A:
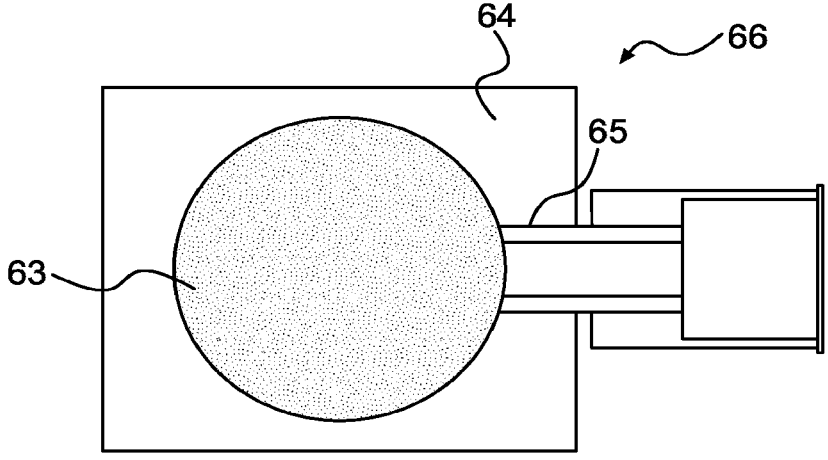
FIGS. 14A and 14B present top views of an embodiment of a flexible pouch with a circular seal. The pouch is bonded and sealed with a needle-free swabable connector at one end.
Figure 14B:
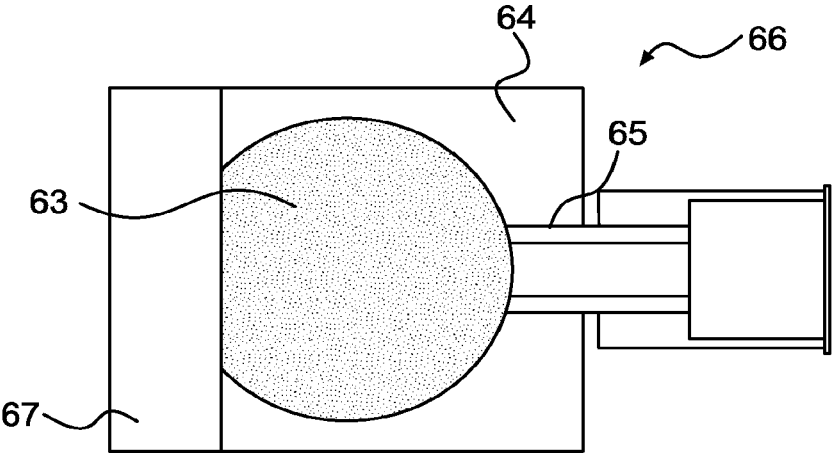

FIGS. 14A and 14B provide another embodiment of the invention in which a flexible pouch (66) may be made from bonding and sealing two layers of polymeric materials to create a circular space. The polymeric material may be bonded and sealed with a needle-free swabable connector (65). The pouch may not have another opening as shown in FIG. 14A, or may have another opening at another end (67) as shown in FIG. 14B. The circular seal is created to accommodate a small volume of tissue and/or cellular material and avoid the dead space that could trap cells or tissues.

Tissue and/or cellular material (63) may be loaded into the pouch from the opening (67). After the tissue and/or cellular material are loaded, additional biological fluids, such as preservation solutions, may be added from either end of the pouch. The opening (67) may then be sealed.

Cellular material and/or biological fluids may also be loaded from the needle-free swabable connector (65). In the case where the cellular material and/or biological fluids are loaded from the needle-free swabable connector (65), the opening (67) may be sealed first, as shown in FIG. 14B, and the fluids or cells may be injected through the needle-free swabable connector (65). The sealed package (66) containing tissue and/or cellular material may be placed in a secondary container and sealed again to further prevent contamination.

Figure 15:
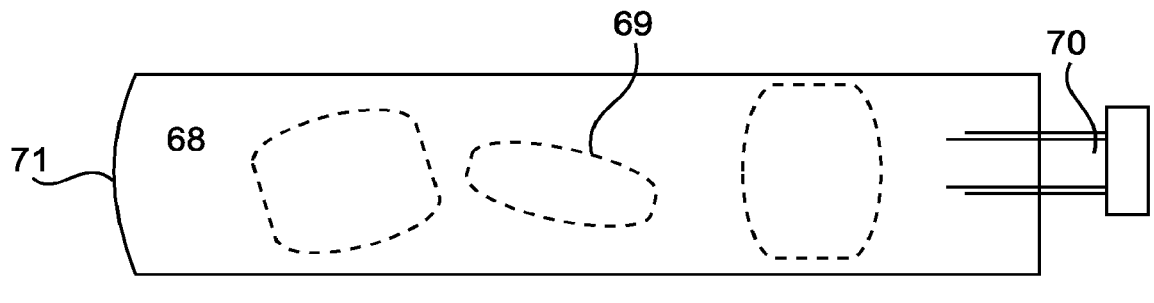
FIG. 15 presents a top view of a flexible outer pouch containing one or more separate inner pouches.

FIG. 15 presents a top view of a flexible outer pouch (68) comprising one or more separate inner pouches (69). The flexible outer pouch may incorporate a port (70) at one end and may be open at the opposite end (71). The port may contain a connector which may be used for allowing mixing and/or extraction of contents by, for example, drawing, squeezing or pumping. The connector may be a luer fitting, a screw thread or a needle port, although these examples are not limiting. The inner pouch or pouches may be used for separating one or more components from other components stored in the outer pouch until mixing of components is required. The outer pouch may be filled from the open end or the port and the open end sealed to contain the one or more components. The inner and outer pouches may be filled with the same or different solutions, solvents or biological materials. One or more of the inner pouches may be made of a biocompatible material that is more easily ruptured than the outer pouch allowing for rupture of one or more of the inner pouches without compromising the integrity of the outer pouch. Rupture of an inner pouch may be achieved by squeezing the inner pouch. The inner pouch or pouches may be made of the same biocompatible material as the outer pouch, or may be of a different biocompatible material than the outer pouch.

Figure 16A:
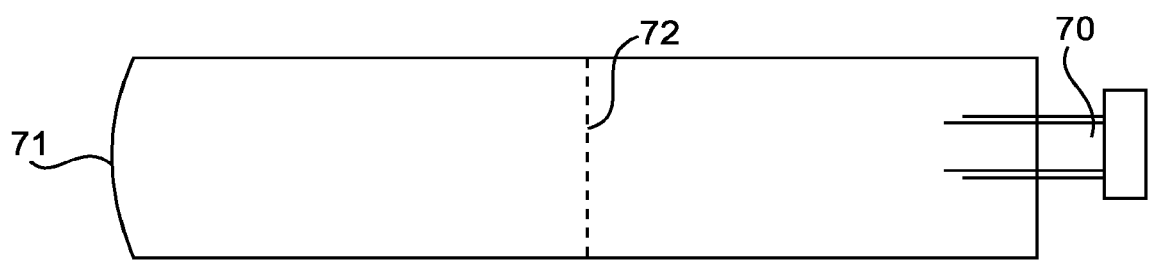
FIGS. 16A and 16B present top views of a flexible pouch divided into two separate compartments by a wall of biocompatible material.
Figure 16B:
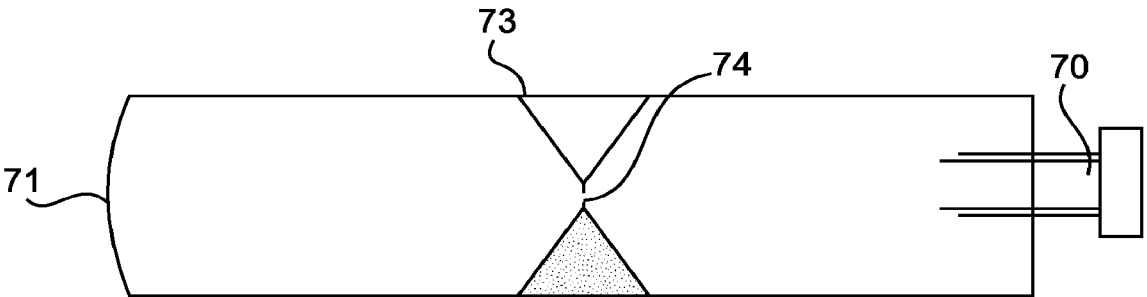

FIGS. 16A and 16B present top views of a flexible pouch divided into two separate compartments by a wall of biocompatible material (72). The flexible outer pouch may incorporate a port (70) at one end and may be open at the opposite end (71). The port may contain a connector which may be used for allowing mixing and/or extraction of contents by, for example, drawing, squeezing or pumping. The connector may be a luer fitting, a screw thread or a needle port, although these examples are not limiting. The dividing wall (72) is designed to be sufficiently weak to be capable of rupturing with the application of pressure on one or both of the compartments. Each compartment may be filled with the same or different solutions, solvents or biological material. The wall material may be made of the same material as the outer pouch or be of a different biocompatible material. Rupturing the wall creates a channel (s) for mixing the components when desired. FIG. 16B includes a feature wherein the pouch layers are pinched and sealed (73) approximately at the mid-point of the pouch to allow for a shorter dividing wall (74) between the two compartments. This feature may be used to decrease the chance of accidental rupture of the wall.

Figure 17:
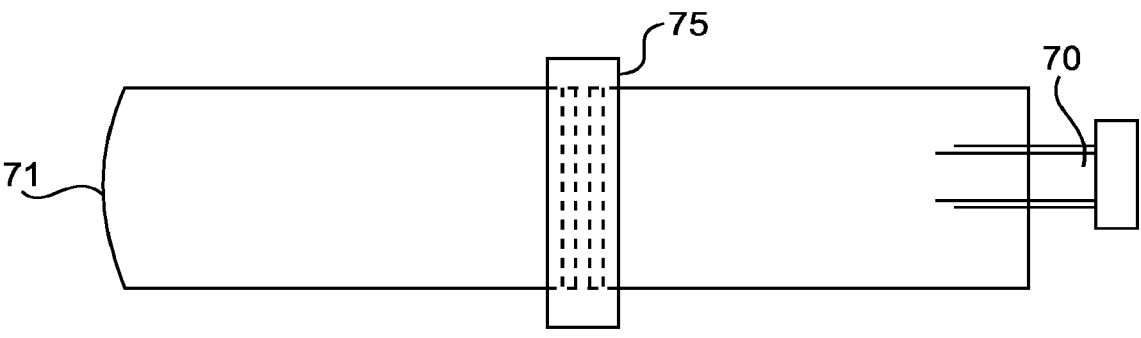
FIG. 17 presents a top view of a flexible pouch divided into separate compartments by application of one or more clamps or clips.

FIG. 17 presents a top view of a flexible pouch that was divided into separate compartments by application of one or more clamps or clips (75). The flexible pouch may incorporate a port (70) at one end and is open at the opposite end (71). The port may contain a connector which may be used for allowing mixing and/or extraction of contents by, for example, drawing, squeezing or pumping. The connector may be a luer fitting, a screw thread or a needle port, although these examples are not designed to be limiting. Each compartment may be filled with a different solution or biological material. The clips maintain separation of two or more components in the pouch. Removal of the clip or clamp allows mixing of the components by massaging the pouch.

The biological fluids or biological solutions of the invention may also comprise bioactive supplements selected from the group which includes, but is not limited to, a growth or differentiation factor of the FGF family, the TGF-family, IGF-1, PDGF, EGF, VEGF, HGF, PTHrP, Ihh, dexamethasone, insulin, transferrin, selenium, ITS, ascorbate and mixtures thereof.

The biological fluids or biological solutions may also comprise bioactive supplements selected from the group which includes, but is not limited to, cytokine of GM-CSF, G-CSF, TNF-$\alpha$, IL-1$\beta$, IL-4, IL-6, IL-8, IL-10, SLP1, MCP1, MIP-1$\alpha$, MIP-2, IL-18, angiopoietin, KGF, endothelin, IFN-$\alpha$, IFN-$\beta$ and mixtures thereof.

The biological fluids or biological solutions may additionally comprise bioactive supplements selected from the group which includes, but not limited to, anti-inflammatory agent of an IL-1$\alpha$R antibody, TNF-$\alpha$ receptor antagonist, cyclooxygenase-2 specific inhibitors, MAP kinase inhibitors, NO synthase inhibitors, NF-$\kappa$B inhibitors, inhibitors of MMP and mixtures thereof.

The biological fluids or biological solutions may also comprise bioactive supplements extracted from tissue selected from the group which includes, but is not limited to, demineralized bone matrix, basement membrane, submucosa matrix and mixtures thereof.

The biological fluids or biological solutions may comprise antioxidants selected from the group that includes, but is not limited to, sodium nitroprusside, cartilage matrix glycoprotein (CMGP), vitamin C, vitamin E, selenium, N-Acetylcysteine (NAC) estradiol, glutathione, melatonin, resveratrol, flavonoid, carotene, aminoguanidine, or lycopene.

The biological fluids or biological solutions may comprise natural and/or synthetic polymers selected from the group which includes, but is not limited to, native or modified collagen, gelatin, agarose, modified hyaluronic acid, fibrin, chitin, biotin, avidin, demineralized bone matrix, Matrigel, extracellular matrix (e.g., human extracellular matrix), proteoglycans, laminin, fibronectin, elastin, heparin, glycerol, sucrose octasulfate, polyethylene glycol, polymethylmethacrylate, polyurethane, acryloilmorpholine, N,N-dimethyl acrylamide, N-vinyl pyrrolidone and tetrahydrofurfuryl methacrylate, hydroxyapatite, cross-linkage or functionalization of hyaluronan-based collagen and alginate, polyurethane, or polylactic acid, and a combination comprising at least one of the foregoing polymers.

In certain embodiments, the packaging assemblies of the invention are useful for storing, distributing, treating, mixing, and dispensing implantable material, said implantable material including, but not limited to, viable tissue, nonviable tissue, dry tissue, wet tissue, soft tissue, bone, tissue derived material, synthetic biomaterial, engineered biomaterial, natural polymers, human cellular material, animal cellular material, stem cellular material, differentiated cellular material and mixtures thereof. In some embodiments, the implantable material is a synthetic material such as tricalcium phosphate, a natural biomaterial such as a collagen-based scaffold, tissue that may be decellularized and freeze-dried or mixtures thereof.

Example 1: Cryopreservation of Viable Bone Chips in a Pouch

Human corticocancellous bone containing viable cells was ground into bone chips with certain particle sizes. The bone chips were then washed and processed to remove blood, immunogenic cells, mesenchymal cells, and maintained viable bone lineage committed cells. The viable bone chips were packaged in a pouch made from fluorinated ethylene propylene (FEP) (see e.g., FIG. 2). The port (9) consisted of FEP tubing fitted with a threaded kynar female luer (9) connected to a swabable connector (10). The length of the pouch was pre-determined based on the volume of the bone chips to be loaded in the pouch in order to provide sufficient empty space in the pouch to accommodate any cryopreservation media, washing solution, or biological fluids. The port was sealed by the swabable valve (4) in the female luer lock connector (10*a*). Viable bone chips were loaded into the pouch from the opening at end (5) of the pouch (see, e.g., FIGS. 2A AND 2B), maintained at 2-8° C., and sealed using a heat sealer at the opening at end (5). At this point, pre-cooled cryopreservation solution in a syringe was injected into the pouch using the connector 10. Visible air bubbles were removed through the same connector (10). Optionally, a cap (11) may be applied to the male luer lock adapter (12). The sealed package was placed into a secondary pouch made from FEP which was sealed again. The entire package was frozen at a controlled freezing rate of about −1° C. per minutes to about-70° C. or lower, placed in a box, and stored in vapor phase liquid nitrogen for an extended period of time. It is understood that the vapor phase liquid nitrogen has a temperature range between about −135° C. and −190° C.

For thawing, the box was removed from the storage tank and the secondary package was peeled off. The sealed package was placed in a sterile container with a sterile isotonic solution (35-39° C., such as 0.9% sterile saline), to thaw viable bone chips quickly. A sterile empty syringe was then connected to the connector (10) and the preservation media was removed. The tissue/cellular material was further washed twice by injecting and removing a Lactaid Ringer's solution containing 5% Dextrose through connector (10). The sealed end of the pouch (5) was cut open and over 90% of the viable bone chips were retrieved from the pouch and placed in a container.

Example 2: Cryopreservation of a Viable Amniotic Membrane Tissue in a Pouch

Human amniotic membrane was isolated from fresh placenta tissue, washed, processed, placed on a sterile nitrocellulose membrane with the epithelium side facing up, and cut to sizes. One sheet of the viable human amniotic membrane (2×4 cm) including nitrocellulose membrane with epithelium layer facing up was added into the pouch through the opening at end (5) of the pouch (see, e.g., FIG. 3A). The length of the pouch was pre-determined based on the size of the sheet to be loaded in the pouch to provide sufficient empty space in the pouch to accommodate any cryopreservation media, washing solution, or biological fluids. The port was then sealed using the swabable valve (4) in the female luer lock connector (2). The viable amniotic membrane was kept at 2-8° C. and sealed using a heat sealer at the opening end (5) of the pouch. A pre-cooled cryopreservation solution in a syringe was then injected slowly into the pouch using the connector (2). The fluid had direct contact with the epithelium side of membrane while the nitrocellulose membrane was in direct contact with the pouch. Visible air bubbles were removed through the same connector (2). Optionally, a cap (11) may be applied to the connector (2). The sealed package was placed into a secondary pouch made from FEP which was sealed again. The entire package was frozen at a controlled freezing rate of about −1° C. per minute to about −70° C. or lower, placed in a box, and stored in vapor phase liquid nitrogen for an extended period of time.

For thawing the tissue, the box was removed from the storage tank and the secondary package was peeled off. The sealed package was placed in a sterile container with a sterile isotonic solutions (35-39° C., such as 0.9% sterile saline) to thaw the viable amniotic membrane quickly. A sterile empty syringe was then connected to the connector (2) and the preservation media was quickly removed. The tissue/cellular material was further washed twice by injecting and removing the Lactaid Ringer's solution containing 5% Dextrose through connector (2). The sealed end of the pouch (5) was cut open and the viable amniotic membrane was retrieved from the pouch.

Example 3: Storage and Delivery of Freeze Dried Corticocancellous and Demineralized Bone Matrix Human corticocancellous bone was ground into bone chips with certain particle sizes. The bone chips were then cleaned, disinfected using AlloWash® Technology and freeze-dried.

Demineralized fiber bone was prepared by cutting cortical bone to produce cut fiber bone having an average length from about 1 mm to about 100 mm. The cut fiber bone was then cleaned and disinfected, and the bone materials were demineralized using PAD® technology to 1-4% residual calcium. The bone fibers were finally washed in ultrapure water, stored frozen at −70° C. in a sterile container, and freeze-dried.

Human corticocancellous and demineralized fiber bone were mixed at a 1:1 volume ratio and packaged in a pouch made from fluorinated ethylene propylene (FEP) (see e.g., FIG. 1). The length of the pouch was pre-determined based on the volume of the bone chips to be loaded in the pouch to provide sufficient empty space in the pouch to accommodate any biological fluids. The port was sealed using the swabable valve (4) in the female luer lock connector (2). The bone matrices were loaded into the pouch from the opening at end (5) of the pouch (see, e.g., FIGS. 1A and 1B) and sealed using a heat sealer at the opening at end (5). Air was then removed through the connector (2) to create a vacuum environment in the pouch. The sealed package was placed into a secondary pouch made from FEP, which was sealed again. The entire package was stored at room temperature (e.g., from about 15-25° C.). The package may be optionally sterilized using gamma irradiation.

Example 4: Storage and Delivery of Freeze Dried Corticocancellous and Demineralized Bone Matrix Human corticocancellous bone was ground into 1-8 mm bone chips. The bone chips were then cleaned, freeze-dried, and sterilized using AlloWash® Technology.

Human cortical bone particles with particle size range from 250 to 1000 micron were cleaned, disinfected using AlloWash® process, and demineralized using PAD® technology to about 1-4% residual calcium. The demineralized bone particles were finally washed in ultrapure water, stored frozen at −70 degree C. in a sterile container, and freeze-dried.

Human corticocancellous and demineralized bone particles were mixed at a 1:1 volume ratio and packaged in a pouch made from fluorinated ethylene propylene (FEP) (see e.g., FIGS. 1A and 1B). The length of the pouch was pre-determined based on the volume of the bone chips to be loaded in the pouch to provide sufficient empty space in the pouch to accommodate any biological fluids. The port was sealed using the swabable valve (4) in the female luer lock connector (2). The bone matrices were loaded into the pouch from the opening at end (5) of the pouch (see, e.g., FIGS. 1A and 1B) and sealed using a heat sealer at this same opening. The sealed package was placed into a secondary pouch made from FEP, which was sealed again. The entire package was stored at room temperature for an extended period of time. The package may be optionally sterilized using gamma irradiation.

Before implantation, the box was removed and the secondary package was peeled off. The sealed package was placed on a sterile field. A syringe containing 0.9% saline was connected to the connector (2), and the saline was injected into the pouch to pre-wet the tissue for about two minutes or more. The saline solution was then removed. A sterile empty syringe was connected to the connector (2) and pulled to remove residual fluids and air to create a vacuum environment in the pouch. A syringe containing autologous bone marrow aspirate (BMA) was connected to the connector (2), and the BMA was injected into the pouch. Due to the vacuum environment in the pouch, the bone matrix may efficiently absorb the bone marrow aspirate and allow an efficient cell attachment on the bone matrix. The BMA was allowed to clot for about 10-20 minutes. The sealed end of the pouch (5) was cut open and the bone matrix containing BMA was able to slide out of the pouch into a container.

Example 5: Package, Storage, and Delivery of Injectable Particulate Dermal Matrix Decellularized human dermis was pulverized to form a fine particulate and then freeze-dried. While decellularized human dermis was used in this particular example, other types of tissue also can be used, including, but not limited to, fascia, tendon, cartilage, muscle, placenta tissue and mixtures thereof. The freeze-dried dermis particulates were loaded into the flexible pouch to fill approximately half the volume of the pouch. The pouch was sealed below the particulate with a first seal locking plastic clip (75) to contain the particulate. FIG. 17 illustrates one embodiment that is useful for this example. The open end of the pouch was filled with phosphate-buffered saline (PBS) and the open end of the pouch was sealed with a second seal. The pouch may be stored at room temperature or at refrigerated temperature (e.g., from about 0° C. to about 25° C.).

Prior to being used in the operating room, the first seal locking clip was removed and the dried dermis particulate was reconstituted in the PBS by massaging the pouch. A 60 cc syringe was attached to the luer-style port on the pouch. The slurry was then drawn out of the pouch using the attached 60 cc syringe. A 20G blunt stainless steel needle was attached to the syringe and the slurry was pushed through the needle.

Example 6: Package, Storage and Delivery of Flowable Dermal Matrices

Acellular human dermis was pulverized to form a fine particulate and then freeze-dried. While acellular human dermis was used in this particular example, other types of tissue also can be used, including, but not limited to, fascia, tendon, cartilage, muscle, placenta tissue and mixtures thereof. The freeze-dried dermis particulate was loaded into the flexible outer pouch (68) that contains two inner pouches (69). Each inner pouch was sealed with isotonic saline. FIG. 15 illustrates one embodiment that is useful for this example. The outer pouch was sealed close to the end of the pouch opening (71). The pouch may be stored at room temperature or at refrigerated temperature (e.g., from about 0° C. to about 25° C.).

Prior to being used in the operating room, the outer pouch was squeezed sufficiently to rupture the wall of the inner pouches thus releasing the saline solution into the freeze-dried dermis particulate. The dermis particulate was then mixed with the saline solution by massaging the outer pouch. A 10 cm long silicone tubing was attached to the luer-style port on the pouch (70). The slurry was then squeezed out of the pouch through the tubing and applied to the field of interest.

Example 7: Package, Storage and Delivery of Shaped Demineralized Bone Sponge Demineralized bone fibers were compressed in a pre-shaped mold to form a sponge. While demineralized bone fibers were used in this particular example, other types of tissue also can be used, including, but not limited to, viable or non viable bone particles, bone sheets, soft tissue, cartilage, and mixtures thereof. FIG. 2 illustrates one embodiment that is useful for this example. The size of the pouch was pre-determined based on the size of the sponge to be loaded in the pouch in order to provide sufficient empty space in the pouch to accommodate any fluids. The port was sealed by the swabable valve (4) in the female luer lock connector (10*a*). The shaped demineralized bone fibers were loaded into the pouch from the opening at end (5) of the pouch (see, e.g., FIGS. 2A AND 2B) and sealed using a heat sealer at the opening at end (5). The pouch may be stored at room temperature or at refrigerated temperature (e.g., from about 0° C. to about 25° C.).

Prior to being used in the operating room, a syringe containing autologous bone marrow aspirate (BMA) or blood was attached to the connector (2), and the BMA or blood was injected into the pouch. The bone matrix may efficiently absorb the bone marrow aspirate and allow an efficient cell attachment on the bone matrix. The BMA was allowed to clot for about 10-20 minutes. The sealed end of the pouch (5) was cut open and the bone matrix containing BMA was able to slide out of the pouch into a container.

It is to be understood that the scope of the present invention is not to be limited to the specific embodiments described above. The invention may be practiced other than as particularly described and still be within the scope of the accompanying claims.

It is to be understood that the scope of the present invention is not to be limited to the specific embodiments described above. The invention may be practiced other than as particularly described and still be within the scope of the accompanying claims.

What is claimed is:

1. A packaging assembly for storing particulate tissue, comprising:

a pouch formed of a flexible polymeric material and defining a compartment, a first end of the pouch configured to be transitioned from an open configuration to a sealed configuration, the first end defining a first opening via which the pouch is configured to receive particulate tissue into the compartment in the open configuration, the pouch defining a second opening opposite the first opening, the particulate tissue having viable cells and disposed within a preservation solution within the compartment; and a port coupled to the pouch such that at least one of a biological solution, a rinsing solution or the preservation solution can be introduced into or withdrawn from the compartment through the second opening via the port without removal of the particulate tissue from the pouch through the port, wherein the pouch is configured, when the first end is in the sealed configuration, to be cut to define a third opening for withdrawal of the particulate tissue from the compartment through the third opening.

2. The packaging assembly of claim 1, wherein the particulate tissue comprises at least one of dermal, fascia, tendon, cartilage, muscle, placenta material or mixtures thereof.

3. The packaging assembly of claim 1, wherein the particulate tissue comprises dermal material.

4. The packaging assembly of claim 1, wherein the particulate tissue comprises fascia material.

5. The packaging assembly of claim 1, wherein the particulate tissue comprises cartilage material.

6. The packaging assembly of claim 1, wherein the particulate tissue comprises muscle or tendon material.

7. The packaging assembly of claim 1, wherein the particulate tissue comprises placenta material.

8. The packaging assembly of claim 1, wherein the preservation solution includes a cryopreservation media.

9. The packaging assembly of claim 1, wherein a wall thickness of the pouch is between about 0.0005 inches and about 0.010 inches.

10. A packaging assembly for storing implantable material, comprising:

a pouch formed of a flexible polymeric material and defining a compartment, a first end of the pouch configured to be transitioned from an open configuration to a sealed configuration, the first end defining a first opening via which the pouch is configured to receive implantable material into the compartment in the open configuration, the pouch defining a second opening opposite the first opening, the implantable material including viable cells and disposed within a preservation solution within the compartment; and a port coupled to the pouch such that at least one of a biological solution, a rinsing solution or the preservation solution can be introduced into or withdrawn from the compartment through the second opening via the port without removal of the implantable material from the pouch through the port, wherein the pouch is configured, when the first end is in the sealed configuration, to be cut to define a third opening for withdrawal of the implantable material from the compartment through the third opening.

11. The packaging assembly of claim 10, wherein the implantable material comprises at least one of bone or cartilage.

12. The packaging assembly of claim 10, wherein the implantable material comprises bone and cartilage.

13. The packaging assembly of claim 10, wherein the implantable material comprises one or more sheets of tissue.

14. The packaging assembly of claim 10, wherein the implantable material comprises a membrane.

15. The packaging assembly of claim 10, wherein the implantable material comprises a sponge.

16. The packaging assembly of claim 10, wherein the preservation solution comprises a cryopreservation media.

17. The packaging assembly of claim 10, further comprising a sealable secondary container within which the pouch is disposed.

18. The packaging assembly of claim 10, wherein a wall thickness of the pouch is between about 0.0005 inches and about 0.010 inches.

19. The packaging assembly of claim 10, wherein the flexible polymeric material includes at least one of polyethylene, polypropylene, or polyester.

20. The packaging assembly of claim 10, wherein the first opening is larger than the second opening.

* * * * *